(12) United States Patent
Hu

(10) Patent No.: US 8,968,678 B2
(45) Date of Patent: *Mar. 3, 2015

(54) MICROFLUIDIC DETECTION OF ANALYTES

(75) Inventor: Celine Hu, Tiburon, CA (US)

(73) Assignee: Headway Technologies, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/536,423

(22) Filed: Jun. 28, 2012

(65) Prior Publication Data

US 2013/0153420 A1    Jun. 20, 2013

Related U.S. Application Data

(63) Continuation of application No. 12/088,636, filed as application No. PCT/US2006/039068 on Oct. 4, 2006, now Pat. No. 8,263,022.

(60) Provisional application No. 60/723,715, filed on Oct. 4, 2005, provisional application No. 60/820,566, filed on Jul. 27, 2006.

(51) Int. Cl.
*G01N 27/447* (2006.01)
*G01N 27/453* (2006.01)

(52) U.S. Cl.
USPC .......................... 422/502; 204/603; 204/453

(58) Field of Classification Search
USPC .................. 204/453, 604, 605; 422/502–508
See application file for complete search history.

(56) References Cited

U.S. PATENT DOCUMENTS

| 4,501,692 A | 2/1985 | Gibbons et al. |
| 5,045,172 A | 9/1991 | Guzman |
| 5,156,810 A | 10/1992 | Ribi |
| 5,340,452 A | 8/1994 | Brenner et al. |
| 5,405,743 A | 4/1995 | Tarnowski et al. |
| 5,605,662 A | 2/1997 | Heller et al. |
| 5,741,639 A | 4/1998 | Ensing et al. |
| 5,965,001 A | 10/1999 | Chow et al. |
| 6,007,690 A | 12/1999 | Nelson et al. |
| 6,042,709 A | 3/2000 | Parce et al. |
| 6,057,167 A | 5/2000 | Shieh et al. |
| 6,068,818 A | 5/2000 | Ackley et al. |
| 6,099,803 A | 8/2000 | Ackley et al. |

(Continued)

FOREIGN PATENT DOCUMENTS

| EP | 1696026 | 5/2007 |
| EP | 1568705 | 10/2008 |

(Continued)

OTHER PUBLICATIONS

Altria, K.D. Overview of capillary electrophoresis and capillary electrochromatography. Journal of Chromatography. 1999, vol. 856, No. 1-2, pp. 443-463.

(Continued)

*Primary Examiner* — J. Christopher Ball
(74) *Attorney, Agent, or Firm* — Michael B. Rubin; Bozicevic, Field & Francis LLP

(57) ABSTRACT

An apparatus and methods for concentrating samples for application to microfluidic devices are disclosed. The methods involve electrophoresing charged molecules from a high volume sample into a smaller volume. The analyte of interest can be a charged molecule or can be modified to be charged using, for example, one or more ionic moieties.

42 Claims, 7 Drawing Sheets

(56) References Cited

U.S. PATENT DOCUMENTS

| | | | |
|---|---|---|---|
| 6,129,828 | A | 10/2000 | Sheldon et al. |
| 6,225,059 | B1 | 5/2001 | Ackley et al. |
| 6,319,472 | B1 | 11/2001 | Ackley et al. |
| 6,331,274 | B1 | 12/2001 | Ackley et al. |
| 6,375,899 | B1 | 4/2002 | Ackley et al. |
| 6,406,604 | B1 | 6/2002 | Guzman |
| 6,475,441 | B1 | 11/2002 | Parce et al. |
| 6,479,644 | B1 | 11/2002 | Bertling |
| 6,533,914 | B1 | 3/2003 | Liu |
| 6,537,433 | B1 | 3/2003 | Bryning et al. |
| 6,540,961 | B1 | 4/2003 | Ackley et al. |
| 6,613,581 | B1 | 9/2003 | Wada et al. |
| 6,695,009 | B2 | 2/2004 | Chien et al. |
| 6,726,880 | B1 | 4/2004 | Ackley et al. |
| 6,767,706 | B2 | 7/2004 | Quake et al. |
| 6,827,830 | B1 | 12/2004 | Slater et al. |
| 6,864,102 | B2 | 3/2005 | Van Damme et al. |
| 6,887,384 | B1 | 5/2005 | Frechet et al. |
| 6,926,313 | B1 | 8/2005 | Renzi |
| 6,929,730 | B2 | 8/2005 | Lee et al. |
| 6,942,771 | B1 | 9/2005 | Kayyem |
| 8,263,022 | B2 | 9/2012 | Hu |
| 2002/0042125 | A1 | 4/2002 | Petersen et al. |
| 2003/0027225 | A1 | 2/2003 | Wada et al. |
| 2004/0062882 | A1 | 4/2004 | Liebmann-Vinson et al. |
| 2004/0175299 | A1 | 9/2004 | Belenky et al. |
| 2004/0188253 | A1 | 9/2004 | Vann et al. |
| 2005/0170362 | A1 | 8/2005 | Wada et al. |
| 2006/0040412 | A1 | 2/2006 | Haik |

FOREIGN PATENT DOCUMENTS

| | | |
|---|---|---|
| JP | 58168957 | 5/1983 |
| WO | WO 0169230 | 9/2001 |
| WO | WO 02059590 | 8/2002 |
| WO | WO 03096016 | 11/2003 |
| WO | WO 2004092733 | 10/2004 |

OTHER PUBLICATIONS

Asbury, C., et al. Trapping of DNA by dielectrophoresis. Electrophoresis. 2002, vol. 23, pp. 2658-2666.

Astorga-Wells, J., et al. Fluidic preconcentrator device for capillary electrohphoresis. Analytical Chemistry. 2003, vol. 75, pp. 5207-5212.

Dai, J., et al. Electrokinetic trapping and concentration enrichment of DNA in a microfluidic channel. JACS. 2003, vol. 125, pp. 13026-13027.

Fa, K., et al. Profiling pH gradients across nanocapillary array membranes connecting microfluidic channels. JACS. 2005, vol. 127, pp. 13928-13933.

Fu, L., et al. Low-voltage driven control in electrophoresis microchips by traveling electric field. Electrophoresis. 2003, vol. 24, pp. 1253-1260.

Galloway, M., et al. Contact conductivity detection in poly(methylmethacylate)-base microfluidic devices for analysis of mono- and polyanionic molecules. Analytical Chemistry. 2002, vol. 74, pp. 2407-2415.

Lin, C., et al. On-line sample concentration techniques in capillary electrophoresis: Velocity gradient techniques and sample concentration techniques for biomolecules. Electrophoresis. 2004, vol. 25, pp. 4058-4073.

Macounova, K., et al. Concentration and separation of proteins in microfluidic channels on the basis of transverse IEF. Analytical Chemistry. 2001, vol. 73, pp. 1627-1633.

Park, S., et al. Concentration of DNA in a flowing stream for high-sensitivity capillary electrophoresis. Analytical Chemistry. 2003, vol. 75, pp. 4467-4474.

Scuor, N., et al. Modeling of a microfluidic channel in the presence of an electrostatic induced cross-flow. Biomedical Microdevices. 2005, vol. 7, pp. 231-242.

Srivastava, A., et al. Numerical simulation of DNA sample preconcentration in microdevice electrophoresis. Electrophoresis. 2005, vol. 26, pp. 1130-1143.

Stellwagen, et al. The free solution mobility of DNA. Biopolymers. 1997, vol. 42, pp. 688-703.

Wainright, A., et al. Sample pre-concentration by isotachophoresis in microfluidic devices. Journal of Chromatography A. 2002, vol. 979, pp. 69-80.

Wainright, A., et al. Preconcentration and separation of double-stranded DNA fragments by electrophoresis in plastic microfluidic devices. Electrophoresis. 2003, vol. 24, pp. 3784-3792.

Yang, H., et al. Sample stacking in laboratory-on-a-chip devices. Journal of Chromatography A. 2001, vol. 924, pp. 155-163.

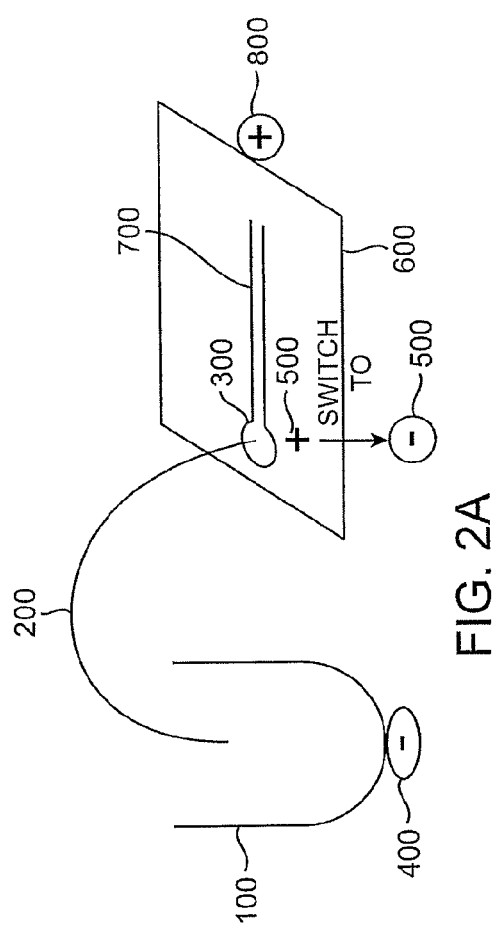
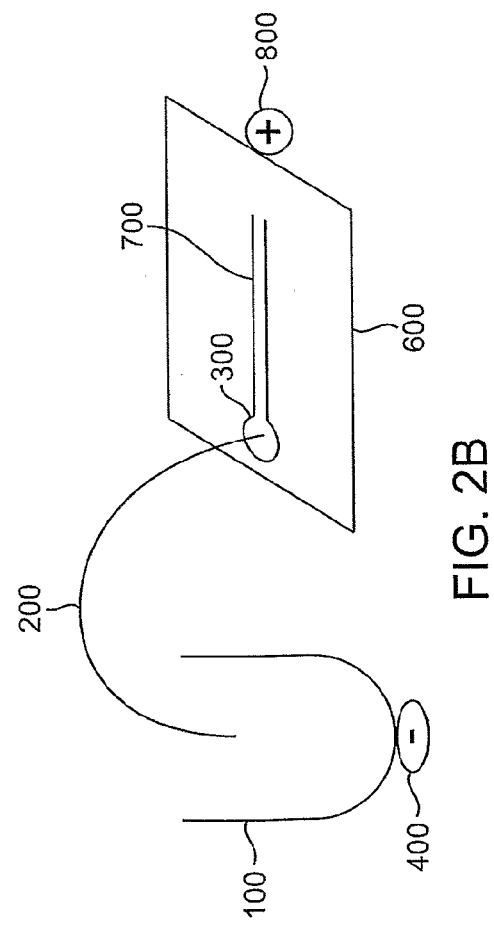
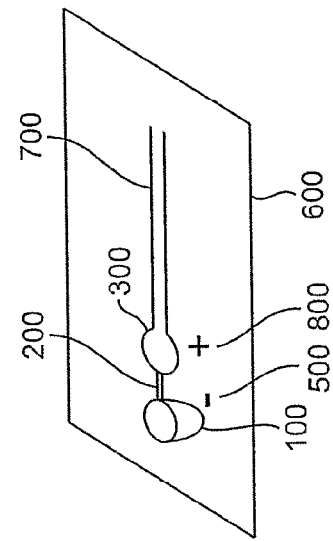
FIG. 2A
FIG. 2B
FIG. 2C

MICROFLUIDIC DETECTION OF ANALYTES

CROSS-REFERENCE TO RELATED APPLICATIONS

This application is a Continuation of U.S. application Ser. No. 12/088,636, filed Mar. 28, 2008, now U.S. Pat. No. 8,263,022, which application is a 371 National Stage Filing of PCT/US2006/039068, filed Oct. 4, 2006, which application claims benefit of U.S. Provisional Application Nos. 60/723,715, filed Oct. 4, 2005 and 60/820,566, filed Jul. 27, 2006, the entire contents of which are incorporated herein by reference.

FIELD OF THE INVENTION

The invention relates to microfluidics and detection of analytes present at low concentrations in a sample.

BACKGROUND OF THE INVENTION

Microfluidic systems have great potential for use in a clinical laboratory setting. However, these devices are limited by the fact that they have capacity for only very small sample volumes, typically on the order of a few microliters or less. When substances to be analyzed are found in a sample at a very low concentration, sensitivity can be limited. One way to overcome this limitation is by using an analyte amplification step to increase the analyte concentration either before or after introduction of the sample to a microfluidic device. For example, very small amounts of nucleic acids can be amplified using methods such as PCR. However, not all analytes can be amplified and, even when possible, amplification may require additional reagents and increase the complexity of analysis. New methods that allow analytes from large volume samples to be assayed in a microfluidic format and/or allow analyses without an amplification step would be valuable for clinical and other laboratory assays. The present invention meets this and many other needs.

BRIEF SUMMARY OF THE INVENTION

In one aspect, the invention provides methods for introducing or applying an analyte of interest in a sample to a microfluidic device by providing one or more aqueous samples in one or more large volume reservoirs, the samples containing the analyte and having a volume of greater than 10 microliters, and the analyte of interest is charged or associated with a charged molecule, such as an ionic molecule or a carrier molecule that is charged. The next steps involve providing a microfluidic device comprising an analysis area, providing one or more connectors, wherein the large volume reservoir(s) and microfluidic device are fluidically connected via the connector, and electrophoresing the analyte from the large volume reservoir to the microfluidic device and through the analysis area for a time sufficient to result in a higher concentration of analyte in the analysis area than the concentration in the large volume reservoir and/or the sample. The large volume reservoir can be a microwell plate, an eppendorf tube, or a test tube. The large volume reservoir can be a well that is integral with the microfluidic device. The connector can be a capillary tubing. In one aspect of the invention, the analyte of interest is a biomolecule, such as a peptide, a protein, a nucleic acid, a lipid or a sugar. The analyte associated with a charged molecule can be, for example, an analyte attached to an ionic moiety or an analyte attached to an antibody that is ionically charged.

In a further aspect of the invention, the sample is first admixed with an antibody and the antibody specifically binds to the analyte of interest. The antibody can be modified with at least one ionic moiety. Alternatively, the analyte of interest can be modified to be charged, for example, with an antibody or an ionic moiety.

In a further aspect, the analysis area is a capture site and the method involves moving the charged molecule(s) across the capture site, the capture site includes at least one capture agent and this allows the analyte of interest to be captured. The movement over the capture area may be by electrophoresis. The method can further include detecting the analyte bound by the capture agent. The capture agent can bind the analyte or ionic moiety. The capture agent may be an antibody or a nucleic acid. The detection can involve detecting a label on the antibody, the analyte, or the ionic moiety.

In a further aspect, the method involves providing a staging reservoir, such that the large volume reservoir and the staging reservoir are fluidically connected via the connector.

In one aspect of the invention, the sample has a volume of from about 20 μl to 50 mls, preferably from 50 μl to 20 mls. Alternatively, the sample has a volume of greater than about 20 μl, preferably greater than about 50 μl.

In one aspect of the invention, the analyte of interest is attached to a microparticle before electrophoresis. The microparticle can be a magnetic microparticle. Preferably, the microparticle is coated with at least one receptor, antibody, or anti-ligand specific for the analyte of interest. The method may include the step of removing the analyte from the microparticle prior to electrophoresis. The antibody can recognizes the analyte. A second antibody can be provided and can bind to a different site on the analyte. The detection can involve detecting a label on the second antibody.

In a further aspect, the ionic moiety can be attached at any step before electrophoresis via an indirect attachment. The indirect attachment can be via an avidin/biotin attachment.

A further aspect is a system for introducing or applying a charged analyte in a sample to a microfluidic device having an analysis area, where the system includes at least one large volume reservoir, operably attached to a first electrode, at least one analysis area, operably attached to a second electrode, and at least one connector for moving charged molecules out of the large volume reservoir, where the large volume reservoir and the analysis area are in fluidic communication. The at least one connector can be capillary tubing. The microfluidic device can include a staging reservoir with a large volume reservoir fluidically connected to the staging reservoir via the connector. The analysis area can include a capture site. The system can include multiple large volume reservoirs fluidically connected to separate staging reservoirs.

BRIEF DESCRIPTION OF THE DRAWINGS

FIGS. 2A-C illustrate three embodiments for the system for concentrating analytes.

FIG. 2A illustrates an embodiment in which the analytes accumulate in a staging reservoir.

FIG. 2B illustrates an embodiment in which the analytes do not accumulate, but there is a continuous flow over the microfluidic device and through the analysis area. FIG. 2C illustrates an embodiment in which the large volume reservoir is integral with the microfluidic device.

DETAILED DESCRIPTION OF THE INVENTION

I. Introduction

Figure 1:
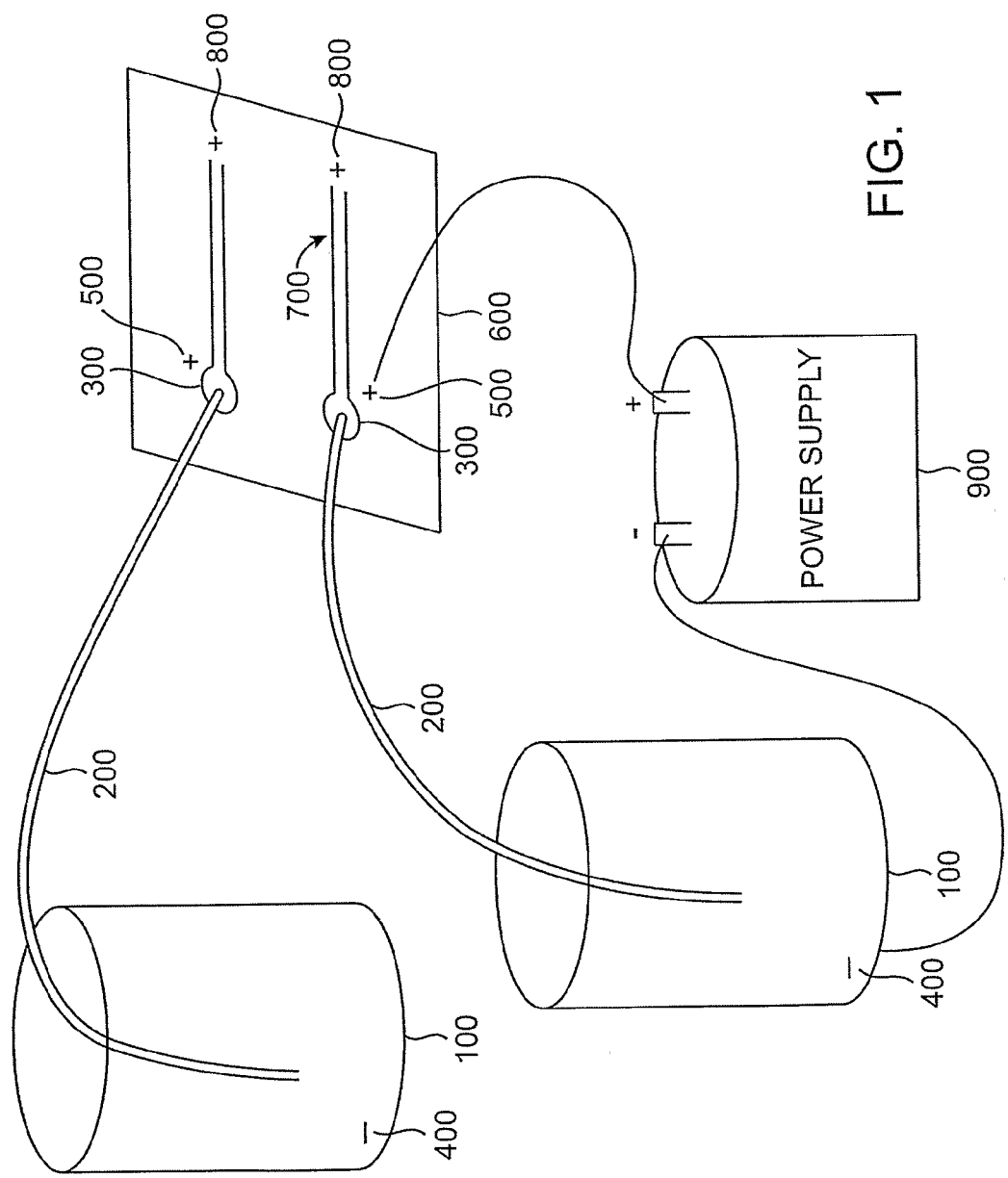
FIG. 1 illustrates a system for concentrating samples for introduction to a microfluidic device.

Microfluidics is the science of designing, manufacturing, and using devices and processes that deal with volumes of fluid on the order of nanoliters or picoliters. Typically, a microfluidic device has at least one channel or vessel with a size less than 1 mm in at least one dimension. The device may have at least one channel or vessel with a size less than 0.5 mm, 0.2 mm, or 0.1 mm in at least one dimension. Microfluidic devices can additionally have micropumps, valves, temperature regulators, etc.

A number of methods and approaches are known form making microfluidic devices, including microassembly, bulk micromachining methods, surface micro-machining methods, standard lithographic methods, wet etching, reactive ion etching, plasma etching, stereolithography and laser chemical three-dimensional writing methods, soft lithography methods, modular assembly methods, replica molding methods, injection molding methods, hot molding methods, laser ablation methods, combinations of methods, and other methods known in the art. It will be apparent to those of skill in the art that a number of these approaches can be adapted for use according to the present invention. For general reviews of microfluidic devices see, for example, Chovan, et al. "Microfabricated devices in biotechnology and biochemical processing" *Trends Biotechnol.* 2002 20:116-22; Anthony et al. "DNA array technology and diagnostic microbiology" *Expert Rev. Mol. Diagn.* 2001 1:30-8; Windman et al. "Microfluidics for ultrasmall-volume biological analysis" *Adv. Chromatogr.* 2003, 42:241-67; and Ng et al. "Biochips beyond DNA: technologies and applications" *Biotechnol Annu Rev.* 2003, 9:1-149; Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rossier et al., 2002, "Plasma etched polymer microelectrochemical systems" *Lab Chip* 2:145-150; Becker et al., 2002, "Polymer microfluidic devices" *Talanta* 56:267-287; Becker et al., 2000, "Polymer microfabrication methods for microfluidic analytical applications" *Electrophoresis* 21:12-26; U.S. Pat. No. 6,767,706 B2, e.g., Section 6.8 "Microfabrication of a Silicon Device"; Terry et al., 1979, A Gas Chromatography Air Analyzer Fabricated on a Silicon Wafer, IEEE Trans, on Electron Devices, v. ED-26, pp. 1880-1886; Berg et al., 1994, Micro Total Analysis Systems, New York, Kluwer; Webster et al., 1996, Monolithic Capillary Gel Electrophoresis Stage with On-Chip Detector in International Conference On Micro Electromechanical Systems, *MEMS 96*, pp. 491496; Unger et al., 2000, *Science* 288:113-16; U.S. Pat. No. 6,960,437 (Nucleic acid amplification utilizing microfluidic devices); Quake & Scherer, 2000, "From micro to nanofabrication with soft materials" *Science* 290:1536-40; Becker et al., 2000, "Polymer microfabrication methods for microfluidic analytical applications" *Electrophoresis* 21:12-26. Also described in the art are microelectrodes suited for use in microfluidic devices. Also described in the art are methods for immobilizing proteins, nucleic acids or other molecules on a surface of the device (e.g., within a microfluidic channel).

Microfluidic devices (sometimes referred to as "chips") can be used in a variety of biomedical and pharmaceutical applications, including analysis, preparation and synthesis of chemical compounds and analysis and manipulation of cells, proteins and nucleic acids. The advantages of miniaturization include greatly reduced consumption of reagents, shorter reaction times, and the potential of very high throughput using massively parallel-testing. However, one aspect of this miniaturization also becomes a significant obstacle that limits the sensitivity of these procedures. Microfluidic chips handle only minute volumes of sample solutions, and there may be insufficient analyte molecules in the very small volume applied to the chip to be readily detected. Thus, an amplification step, such as PCR, is often used to treat the sample for use with a microfluidic device, either before or after introduction of the sample to the device. However, this has the disadvantage of increasing the cost and complexity, and allowing possible aberrant results due to PCR mistakes. Some microfluidic devices are designed to receive a somewhat larger sample volume by exposing the entire surface of the chip to the incoming sample solution. This allows a relatively large sample volume to be applied since the whole chip surface is used to receive the sample, but still limits the volume of the sample that can be processed. Moreover, this limits the detection to one sample at a time and requires different sample solutions to be tested sequentially. For testing multiple samples, this is not only time-consuming, but has the additional disadvantage of risking sample-to-sample cross-contamination.

The methods and apparatus disclosed herein overcome the limitation of low volume capacity on microfluidic devices by using electrophoresis to concentrate and/or control the transport of the analyte material, so that it can be applied to facilitate reactions or analysis and used in a typical chip format. The analyte is electrophoresed through an aqueous buffer solution without the use of size exclusion gels, a viscous medium, filters, biological sieves or the like. The method allows multiple samples to be applied to multiple specific areas on the chip. Because each sample is separately electrophoresed to a different part of the chip for analysis, separate samples do not come in contact with the same surface. This has the advantage of reducing cross-contamination.

The invention provides methods and devices for microfluidic analysis of one or more analytes from a large volume sample. Because the sample volume capacity of a device is increased by the methods disclosed herein, the minimal detectable concentration (the lowest analyte concentration the assay can reliably measure) for an assay using the device is reduced.

The methods and devices described herein allow the investigator or clinician to extract analyte from a large volume sample, detect and identify the analyte. The method is suitable for use with a wide variety of analytes, including specific proteins and polynucleotide sequences. In addition to the ability to analyze multiple samples on a single chip simultaneously, embodiments of the method allow for concentration of a large sample onto the chip without continuously flowing the sample into the concentration reservoir or onto the chip.

FIG. 1 is provided to aid in the understanding of the invention. It will be appreciated that FIG. 1 is for illustration and is not intended to limit the invention in any fashion. The system shown in FIG. 1 includes a large volume reservoir (LVR) 100 into which a sample containing an analyte at low concentration can be introduced, a staging reservoir 300 integral to the microfluidic device 600 (sometimes referred to as a "chip"), a connector 200 through which an analyte in the large volume reservoir can be electrophoretically transported to the staging reservoir, and an analysis area 700 in which an analyte can be detected. Generally, the analysis area is a microfluidic channel through which analyte-containing fluid can flow and/or which may contain an aqueous buffer solution through which analyte can be transported. Alternatively, the analysis area can be a well or chamber comprising immobilized capture agents. In some embodiments at least a portion of the housing or material surrounding the analysis area is transparent, to facilitate detection of signal from the analysis area (e.g., fluorescence emissions) As with the connector, the aqueous solution through which analyte is transported into the analysis area generally does not contain exclusion gels, a viscous medium, filters, sieves, etc. for separation of analyte. Electrodes 400 and 500 are positioned so that when electric potential is applied to the electrodes (i.e., a positive charge is applied to one electrode and a negative charge is applied to another) charged analyte is transported through solution to the appropriate region of the device (e.g., staging reservoir). Additional electrodes 800 may optionally be positioned to transport analyte into the analysis area 700. In some embodiments staging reservoir electrodes 500 are not included. Electrodes can be integrated into the LVR or staging reservoir or may be external electrodes placed into the reservoir chamber in contact with the sample or other solution. Battery 900 is any power supply or source of electric current suitable for electrophoresis (for simplicity, in FIG. 1 only one LVR is shown connected to the battery).

The analysis area typically includes "capture agents" associated with the substrate in the analysis area of the device. Capture agents (discussed in detail below) are agents that specifically bind to an analyte, a carrier molecule, an ionic moiety, or other molecule associated with the analyte). Examples of capture agents include antibodies and polynucleotides. Typically the capture agents are immobilized at a "capture site" in the analysis area (a physical surface of the microfluidic device that is capable of being modified by the binding of at least one capture agent, preferably at least two, and more preferably an array of capture agent molecules). Alternatively, in other embodiments, the analysis area does not include a capture agent and the sample is analyzed (detected) as it flows through a detector.

In the operation of the system, a sample solution (e.g., an aqueous liquid that contains, or is suspected of containing the analyte) is introduced into large volume reservoir 100. The large volume reservoir or reservoirs may be integral to the microfluidic device 600, not integral but physically attached to the microfluidic device, or not integral and not attached but placed near the device. For example, the large volume reservoir or reservoirs can be one or more separate containers, such as any of a variety of containers for holding liquids, including but not limited to: a test tube, a microfuge tube, a well of a microwell plate, a tissue culture dish, and the like. The liquid capacity of the large volume reservoir can range from about 10 µl to about 100 mls, and may be at least 10, at least 25, at least 50, at least 100, at least 200, at least 500, at least 1000 or at least 5000 microliters. The liquid capacity of the LVR is most often a range of about 100 ul to about 2 mls. One or more large volume reservoirs can be associated with a single chip. In some embodiments 2, 3, 4, 5, 6, 7, 8, 9, 10, 11, 15, 20, 25, 30, 35, 40, 45, 50, 55, 60, 65, 70, 75, 80, 85, 90, 95, 100, 110, 120, 130, 140, 150, 160, 175, 200, 250 or more large volume reservoirs are associated with a single device. For example, if a microtiter plate is used having 100 wells, the number of large volume reservoirs can be 100.

In accordance with the invention, the analyte is electrophoretically transported via the connector 200 to the staging reservoir 300. Electrophoresis refers to the movement of charged molecules or particles in solution in response to an electric field. The mobility of the analyte is based on (1) a net charge of the analyte molecule itself and/or (2) a net charge of an ionic moiety associated with the analyte, as described below. A net charge is the combination ionic charge that a molecule has, it can be positive negative or neutral. As noted above, the analyte may be electrophoresed through an aqueous buffer solution without the use of size exclusion gels, a viscous medium, filters, biological sieves or the like. As used herein, the phrase "electrophoresis through an aqueous solution" is used to mean that no size exclusion medium or filters are used.

The connector 200 through which the analyte travels can have any of a variety of forms and be made of any material compatible with the analyte and which does not interfere with movement of the charged analyte and/or the electrophoresis. Methods for connecting external sources or tubing to microfluidic devices are known and can be used in the present invention to connect. In some embodiments, the connector has multiple regions with different dimensions. To connect between the large volume reservoir and the staging reservoir or the analysis area the connector 200 may have sections of decreasing diameter. It can be formed by connecting straight or tapered tubes or channels of decreasing diameters and of different materials. In some embodiments in which the LVR is not integral to the chip a portion of the connector may comprise a tube portion through which the analyte is transported from the large volume reservoir to a channel in the microfluidic device, and a portion of the connector may comprise a microfluidic channel on the chip ("microfluidic channel portion of the connector") with the analyte then being transported via the channel to the staging reservoir 300. The channels can be manufactured to have various shapes and dimensions using, for example, well developed elastomer molding, photolithography or micro-machining methods. In some embodiments the connector is entirely off-chip. In one embodiment, the large volume reservoir is integral to the device and connector 200 is a microfluidic channel integral to the microfluidic device.

For tubing, there are also a wide variety of sizes and materials to select from. Examples of methods for forming these types of connectors can be found, for example, in Douglas Smith, Engineering and Science, published by California Institute of Technology, 2003 volume LXVI, Number 2, page 8-18; Skelley A M et al., Proc Natl Acad Sci U S A. 2005 Jan. 25; 102(4):1041-6; Manz, A. and Becker, H., "Microsystem. Technology in Chemistry and Life Sciences" published by Springer-Verlag, 1999. Exemplary tubes include stainless steel tubes, needles, tubings made of plastic material such as polypropylene, polytetrafluoroethylene, Teflon, polyvinylchloride, PEEK™ or PEEKsil™, fused silica or glass. Suitable tubing usually has an inner diameter from several millimeters to microns, including but not limited to about 10 mm, 9 mm, 8 mm, 7 mm, 6 mm, 5 mm, 4 mm, 3 mm, 2 mm, 1 mm, 0.5 mm, 0.1 mm, 90 µm, 80 µm, 70 µm, 60 µm, 50 µm, 40 µm, 30 µm, 20 µm, 10 µm, 9 µm, 8 µm, 7 µm, 6 µm, 5 µm, 4 µm, 3 µm, 2 µm, 1 µm. Often the inner dimensions of a connector are in the range of 5 mm to 50 µm.

The staging reservoir 300, if present, is integral to the microfluidic device and typically has a capacity of from about 0.1 pl to about 2 including, but not limited to 1 pl to 1 µl, and 10 pl to 0.5 µl. The staging reservoir is in fluidic communication with the analysis area of the device, such that an analyte can be transported from the staging reservoir to the analysis area when appropriate gates or valves are open. The ratio of the volumes in the large volume reservoir and the staging reservoir can range considerably, but in some embodiments, the ratios are from about 100:1 to 1000:1, including but not limited to, more than 100:1, more than 200:1, more than 300:1, more than 500:1, more than 800:1, and more than 1000:1.

To generate the electric field necessary for transport of the analyte from the large volume reservoir to the staging reservoir, electrodes are situated to generate such a field. Typically electrodes are situated within each of the reservoirs (i.e., the LVR and the staging reservoir). The location of the electrode in the LVR may vary, but is preferably some distance from the opening of the connector 200, and preferably at the furthest site or distance from the opening. The electrodes can be attached or positioned in any way that allows an electric field for electrophoresis to be generated when the current is on and solution is present to complete a circuit. For example and not limitation, electrodes can be inserted into the liquid in a reservoir. Alternatively, the electrode can be integral to the chamber or microfluidic device (e.g., incorporated into the wall of a reservoir or chamber). Microelectrodes are well known in the art (see, e.g., International Patent Publication WO04044575A2; Rongsheng et al., 2005, *Anal. Chem* 77:4338-47; Abad-Villar et al, 2005, *Electrophoresis* 26:3602-3608).

In addition, the polarity of electrodes in the device or system can be changed (e.g., from a negative to a positive charge) during the operation of the device. A charged analyte migrates away from an electrode(s) of like charge towards an electrode(s) of opposite charge. Thus, for example, a negatively charged analyte can be transported by electrophoresis from a LVR having a positively charged electrode (anode) to a staging reservoir having a negatively charged electrode (cathode). The analyte can then be transported from the staging reservoir to an analysis area by turning off current to the LVR electrode, changing the polarity of the staging area electrode to positive, and turning on an electrode positioned in or beyond the analysis area, such that the analyte is transported through or across the analysis area. The rate of migration depends on the strength of the field, the net charge, the size and shape of the molecules and also on the ionic strength, viscosity and temperature of the medium in which the molecules are moving.

FIGS. 2A-C illustrate other embodiments of the system. FIG. 2A illustrates an embodiment in which the analyte accumulates in a staging reservoir 300. In this embodiment, the electrode 500 on the microfluidic device 600 can switch from positive to negative as needed. For example, when a negatively charged analyte is being concentrated or accumulating in the staging reservoir 300, the electrode 500 is positively charged. Then in order to electrophorese the analyte to the analysis area 700, the electrode is negatively charged and electrode 800 by the analysis area is positively charged. FIG. 2B illustrates an embodiment in which the analytes do not accumulate in a staging reservoir 300, but are continuously flowed over the microfluidic device 600 and through or to the analysis area 700. FIG. 2C illustrates an embodiment in which the large volume reservoir 100 is integral with the microfluidic device 600, and is connected to the staging reservoir by connector 200.

Reagents used for capture and analysis of the analyte may be prepositioned in channels of the microfluidic device (e.g., capture agents immobilized on the analysis area substrate), may be introduced from the large volume reservoir along with the analyte, or may be introduced on the chip. For example, reagents can be introduced into the staging reservoir, analysis area, or channels by art known methods at any point appropriate for the assay. Methods for introduction will vary with the specific design of the device. For illustration, reagents may be introduced into the analysis area via an input channel in fluidic communication with the analysis area by opening a valve that separated the input channel and analysis area.

II. The Analyte

The analyte (or "analyte of interest") is a molecule, complex of molecules or particle that is measured or detected using the methods and devices of the invention. As noted above, an analyte has a net charge and/or can be associated with a charged molecule, so that the analyte can be electrophoretically concentrated as described herein. In one embodiment the analyte is associated with one or more ionic moieties, which carry a charge. Alternatively, the analyte can be associated with a charged molecule by binding to a charged carrier molecule, such as an antibody, a receptor, a ligand, a substrate, or an antigen. The carrier molecule can be intrinsically charged or can be modified to be charged by attaching an ionic moiety.

Examples of analytes include, but are not limited to, proteins, protein complexes, viruses, nucleic acids, heavy metals, drugs, steroids, and pesticides, and carbohydrates. Preferably, the analytes are biomolecules (a class of molecules that are produced in or by a cell) such as proteins, peptides, polynucleotides (e.g., RNA or DNA), sugars, lipids, glycolipids, glycoproteins, and the like. Particular examples of analytes include biomolecules from pathogenic organisms such as viruses or bacteria, biomolecules associated with disease, toxins, drugs, small molecules, prions, nucleic acids containing mutations, antibodies, and antigens. Analytes that may be analyzed using the method of the invention may or may not have a net charge under the conditions (e.g., pH) of the assay. A polynucleotide is an example of an analyte that is itself charged. An analyte, whether charged or not, can be modified by attachment of at least one ionic moiety, to increase its charge. For example, an analyte can be modified by attachment of a carrier molecule that carries an ionic moiety (for example, an antibody that carries a nucleic acid ionic moiety). Examples of ionic moieties are described below.

III. The Sample Solution and Pre-Sample

As used here, the "sample solution" is the analyte-containing aqueous liquid that is present in the large volume reservoir at the start of electrophoresis (i.e., the "starting material"). In general, the sample solution is generated by processing a "pre-sample" that contains the analyte. Such processing is carried out to, for example, partially purify or concentrate the analyte, remove impurities that would interfere with electrophoresis or the assay, and the like. Examples of specific processing steps include centrifugation (to remove debris, or to fractionate the presample), precipitation, filtration, chromatography, sonication, or any other process that results in analyte free in solution. In one embodiment, processing includes concentration of the analyte using beads, such as magnetic beads, treated to bind the analyte. In addition, reagents may be added to the sample solution to adjust the pH, ionic strength and/or composition of the solution to facilitate electrophoresis by, for example, adding buffering agents, acids, bases or salts. Addition may entail, for example, diluting the analyte-containing liquid with an appropriate solution such as water or buffer (e.g., a buffered salt solution), resuspending the analyte in an appropriate solution, dissolving solids (e.g., salts) in the solution, and the like. In addition, the analyte in the sample solution may be modified by being associated with one or more ionic moieties, and optionally one or more carrier molecules.

The source of analyte can be any of a wide variety of materials, including for example, a biological fluid, cell, or tissue, environmental sample (e.g., soil or water) or a synthetic product. Examples of biological pre-samples include, for example, blood, plasma, cerebro-spinal fluid, urine, saliva, cell extracts, tissue extracts, tissue culture extracts, cell extracts, cheek scrapings, and bacterial or viral cultures. Other examples of pre-sample includes lake or river water, food processing fluids, manufactured food preparations, fruit and vegetable extracts, and cosmetics. The presample can be a liquid or a solid. If a solid, the presample is dissolved, solubilized or suspended in a liquid (e.g., aqueous liquid) and insoluble materials may be removed. Table 1 shows, for illustration and not limitation, exemplary samples and pre-samples.

TABLE 1

Exemplary Samples and Pre-samples

| Pre-sample | Sample | Analyte |
| --- | --- | --- |
| blood | serum* | anti-HIV antibody** |
| urine | filtered urine* | hCG** |
| river water | filtered water* | cholera bacteria antigens** |
| PBMC | genomic DNA | DNA fragment** |

*In each case, modified to adjust ionic strength/pH
**In each case optionally modified to associate with an ionic moiety.

IV. Association of the Analyte with an Ionic Moiety

An ionic moiety is a molecular structure that carries a charge. The ionic moiety can be anionic (e.g., polyanionic) or cationic (e.g., polycationic). It will be appreciated that the net charge of a charged molecule will depend in part on the environment, particularly the pH and salt composition of the sample solution. However, preferably the ionic moiety has a net charge of at least +5 or at least −5. Although the ionic moiety may have a low or medium charge density, preferably the ionic moiety has a high charge density. Charge density is the amount of charge/per unit volume of a solution, material, etc due to the presence of charged entities within the material. A material having a high charge density has more charge per unit volume, and is more likely to attract entities having an opposite charge, and repel entities having the same charge. Typically having a higher charger density will likely result in faster migration times of a charged entities during electrophoresis.

Examples of ionic moieties include, for illustration and not for limitation, nucleic acids and their natural and synthetic analogs (e.g., RNA, DNA, PNA), poly-amines such as poly-lysine, poly-glutamate, poly-aspartate, sulfated glycans and chemically modified proteins such as succinylated bovine serum albumin. Other ionic moieties include polyacrylic acid, polymethacrylic acid, polyethylacrylic acid, polypropylacrylic acid, polybutylacrylic acid, polymaleic acid, dextran sulfate, heparin, hyaluronic acid, polysulfates, polysulfonates, polyvinyl phosphoric acid, polyvinyl phosphoric acid, copolymers of polymaleic acid, polyhydroxybutyric acid and mixed polymers.

V. Association of the Analyte with an Ionic Moiety

Prior to electrophoresis, the analyte can be modified to be associated with an ionic moiety. The combination of the analyte and ionic moiety typically has a net charge greater than that of the analyte alone. The analyte can be modified directly with the ionic moiety or indirectly using a carrier molecule that carries an ionic moiety. Carrier molecules include analyte-binding antibodies, polynucleotides and other molecules, as discussed below.

A. Direct Association of an Ionic Moiety and Analyte

In some cases, an ionic moiety is associated directly, either covalently or noncovalently, with the analyte. For example, a nucleic acid ionic moiety may be noncovalently associated with a nucleic acid analyte based on sequence complementarity (partial or complete). The analyte can also be covalently modified to increase its ionic charge either chemically or enzymatically. Examples of chemical modifications include converting amino groups in a protein to carboxyl groups to increase the net negative charge of the protein using reagents such as anhydrides (e.g., succinic anhydride or tetrahydrylphthalic anhydride). Other groups in a protein such as thiol or histidyl groups can also be converted to negatively charged groups such as carboxyl groups using reagents such as iodoacetate. In addition, these functional groups can be converted to a number of other active groups to facilitate the association of ionic moieties. These and other modification reagents and modificaiton methods are known in the art (see, e.g., "Chemical Modification of Proteins" by Gary E. Means and Robert E. Feeney; "Bioconjugate Techniques" by Greg T. Hermanson; and "Chemical Reagents for Protein Modification" by Roger L. Lundblad).

Certain ionic moieties, such as nucleic acids, poly-lysine, poly-arginine, poly-glutamate, poly-aspartate and sulfated glycans, have functional groups (such as amino or carboxyl groups) that can facilitate covalent association with the analyte. Moreover, ionic moieties can be derivitized by design to have desirable functional groups for conjugation with the analytes.

In addition, a number of commercially available cross-linking agents are known which can be used to attach carrier molecules and ionic moieties (e.g., homo-bifunctional reagents that will cross-link amino-to-amino or sulthydryl-to-sulfhydryl groups; hetero-bifunctional reagents that will cross-link the amino-to-sulfhydryl groups, and the like). These and other cross-linking methods are well known to practitioners in the field and selection can be based on the specific requirements of the assay.

B. Association of an Ionic Moiety and Analyte Indirectly Via a Carrier Molecule or Carrier Complex An analyte also can be associated with an ionic moiety indirectly, via a carrier molecule or carrier complex. A carrier molecule is a molecule that specifically binds the analyte. Thus, the analyte and carrier molecule together constitute a "specific binding pair" or carrier complex. In this embodiment, the ionic moiety is linked or conjugated to the carrier molecule instead of, or in addition to, the analyte. Examples of binding pairs include but are not limited to, antibody-antigen pairs, receptor-ligand pairs, and other ligand:antiligand complexes. Typically the carrier molecule is an antibody that specifically binds the analyte.

TABLE 2

Exemplary Specific Binding Pairs

| Analyte | Carrier Molecule |
|---|---|
| antigen (e.g., protein) | antibody |
| antibody | antigen |
| polynucleotide strand | complementary polynucleotide strand |
| ligand (e.g., hormone) | receptor (e.g., hormone receptor) |
| immunoglobulin | Protein A |
| enzyme | enzyme cofactor or substrate |
| carbohydrate | lectin |

The carrier molecule can be associated with an ionic moiety using any of a variety of methods for associating molecules some of which are discussed above. The selected methods will depend in part on the nature of the analyte, ionic moiety and carrier molecule. For example, one or more ionic moieties can be attached to carrier molecules using standard chemistry. For example, ionic moieties such as nucleic acids, poly-lysine, poly-arginine, poly-glutamate, poly-aspartate and sulfated glycans have functional groups (such as amino or carboxyl) that facilitate cross-linking to antibodies or other carrier molecules, or can be derivitized to carry such functional groups. Some potential carrier molecules, such as nucleic acids and proteins have functional groups (such as amino [e.g., lysine, arginine], carboxyl [e.g., aspartic acid, glutamic acid] or sulfhydryl [e.g., cysteine]) that facilitate cross-linking to ionic moieties, or can be derivitized to carry such functional groups. The carrier molecules can be associated with the ionic moiety or moieties using various bi-functional linkers. Carrier molecules can be chemically modified to have specific functional groups for cross linking. For example, the sulfated glycans can be oxidized to have aldehyde functional groups, which can be used to react with amino groups. Oligonucleotides are synthesized with a sulfhydryl or a primary amino group on one end. With the amino or sulfhydryl functional groups, the oligonucleotide can be cross-linked to the amino or sulfhydryl groups on the antibody molecules using available cross-linking reagents.

The ionic moiety can also be associated with the carrier molecule (and thus the analyte) indirectly, via one or more intermediate molecule. For example, if the analyte is an antigen, "AntigenA," it can be indirectly associated with an ionic moiety by, for example, binding AntigenA by an anti-AntigenA monoclonal antibody (AAA-mAb) ("carrier molecule") and binding the AAA-mAb with an ionically-labeled second antibody (anti-AAA-mAb). It will be recognized that this type of second-antibody type labeling is routine in immunoassays. The complex of molecules comprising the analyte and ionic moiety (in this example, AntigenA+AAA-mAb+anti-AAA-mAb-ionic moiety) can be referred to as a "carrier complex." Although antibody-antigen associations are described in this example, the method is not limited to antibodies. Any specific binding pair in which one of the partners is the analyte may be used.

A carrier molecule and ionic moiety also can be associated via a specific binding pair where one or both members of the specific binding pair is conjugated to a tag. For example, a carrier molecule can be biotinylated and labeled using an ionic moiety conjugated to avidin. The tag is either avidin or biotin and allows binding of the ionic moiety via the tag at any step in the process. In another embodiment, an antibody carrier molecule is associated with an ionic moiety (nucleic acid) as follows: A charged avidin molecule is prepared by adding 1, 2, or 3 biotinylated oligonucleotides to its four sites biotin binding sites, leaving at least one remaining biotin site unoccupied. A biotinylated carrier molecule (e.g., anti-analyte antibody) is bound to the avidin-biotin-oligonucleotide complex. Other examples of tags include without limitation polyhistidine tag, Glutathione tag, digoxin, and fluorescein. Antibodies with specific affinity for the tags are available for purchase or can be produced as needed.

Any of the methods described above in the context of ionically labeling a carrier molecule, can be used to ionically label a protein, nucleic acid, or other component of the carrier complex.

A molecule that is bound directly (e.g., covalently) to an ionic moiety can be referred to as "ionically labeled." The complex of the analyte, associated ionic moiety(s), carrier molecule(s), if present, and any other molecules used to associate the ionic moiety(s) and analyte can be referred to as the "Analyte-Ionic Moiety (IM) complex."

It will be appreciated that the association of the analyte and ionic moieties is sufficiently stable under the conditions of concentrative electrophoresis and, optionally, subsequent concentration analytical steps that the two remain associated as the assay is conducted.

VI. Association of an Ionic Moiety with an Immobilized Analyte

In one aspect the invention provides a method of the invention that makes use, in part, of the concentrative electrophoresis technology described above. According to the method, the analyte is:

a) bound to a solid or immobilized phase
   b) associated with an ionic moiety
   c) released from the solid or immobilized phase
   d) electrophoresed to the microfluidic device
   e) bound or detected in an analysis area using a capture agent that specifically recognizes
      i) the analyte or
      ii) the ionic moiety.

Figure 5:
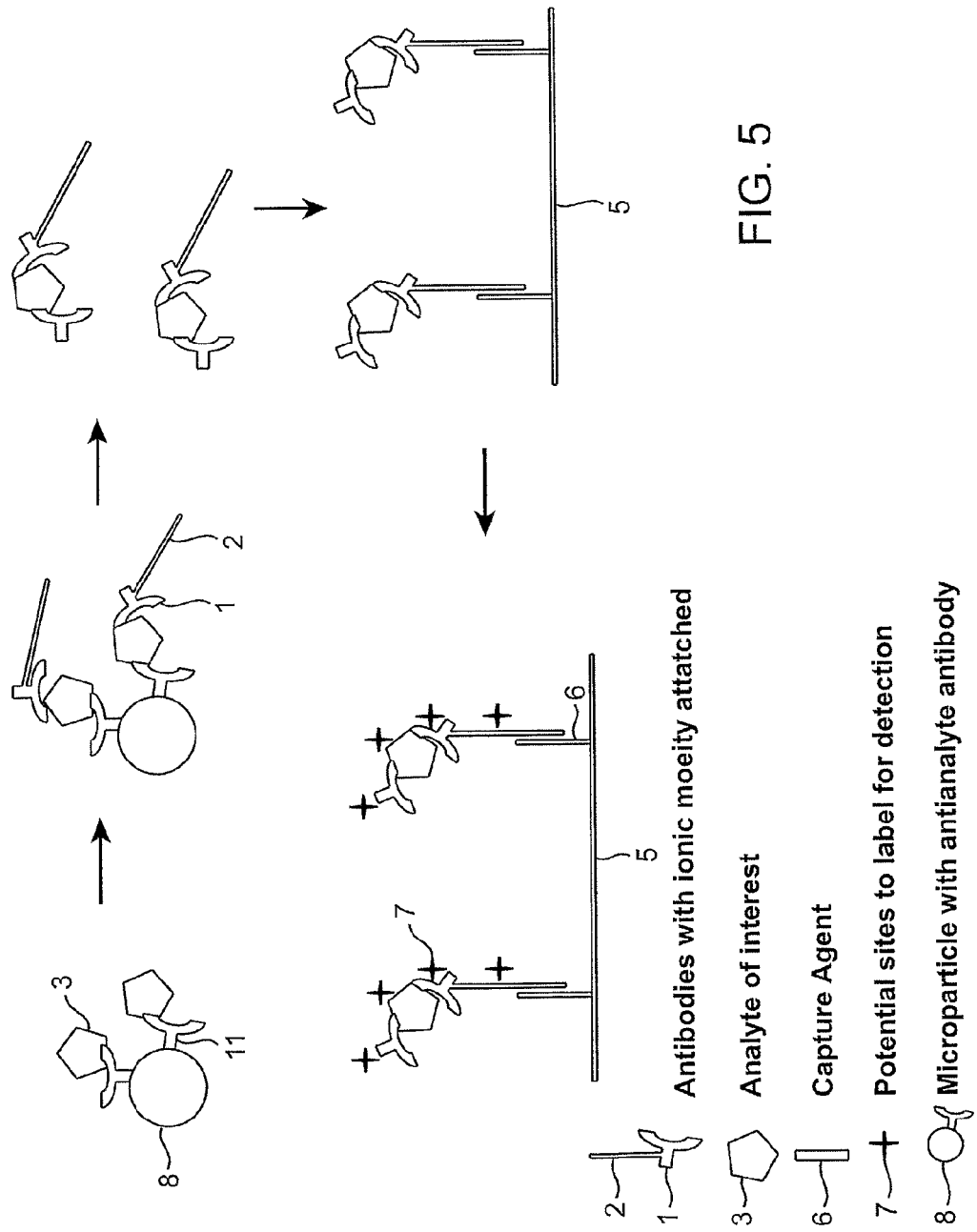
FIG. 5 is a diagram illustrating an embodiment of the invention in which microparticles to which primary antibodies are bound are used as a solid phase to bind analyte in a large volume reservoir. A second antibody, tagged with an ionic moiety, is added and also binds to the analyte. The primary antibodies are cleaved to release the analyte complex from the microparticles, and the complex is electrophoresed into a staging reservoir. The complex is captured on the microfluidic device using a capture agent specific for the ionic moiety.

Steps (a) and (b) can take place in either order and Steps (b) and (c) can take place in either order, provided (c) occurs after (a). For example, the order can be a→b→c; b→a→c; or a→c→b. Steps (a)-(c) are described below, for illustration and not for limitation. Particular embodiments of this method are shown in FIG. 5, and are discussed in the corresponding text. This method includes two independent specific analyte concentration steps and provides a highly sensitive assay method.

a. Analyte is Bound to a Solid or Immobilized Phase

The analyte may be bound to a solid or immobilized phase (used interchangeably herein) in any conventional way, by treating the sample solution with a specific binding partner (SBP) of the analyte immobilized on a solid phase. The solid phase may be, for illustration and not limitation, a surface of the large volume reservoir, a surface of a microtiter plate well, or a surface of a microparticle. In a preferred embodiment, microparticles are used. In one embodiment, magnetic microparticles are used.

Microparticles useful for purification are well known in the art. Microparticles are generally spherical particles typically having a diameter of from about 0.05 μm to about 1000 μm, on which a SBP (e.g., antibody, polynucleotide) can be bound or coated. Microparticles can be manufactured using materials such as glass, zirconium silicate, silica, gold, polystyrene, latex, and PMMA, and may have physical characteristics such as being magnetic or magnitizable, dyed, biodegradable and fluorescent. Microparticles can be coated with a binding agent, or can include reactive groups (e.g., amino, carboxyl, cyanuric) that allow covalent attachment with a binding partner (e.g., antibody, polynucleotide, avidin). In addition, microparticles can be purchased with bound SBPs (e.g., microparticles coated with streptavidin, antibodies to human IgG and IgM, and anti-biotin antibodies from e.g., Indicia Biotechnology (Oullins France)]; microparticles with binding groups: avidin, streptavidin, protein A, albumin, biotin, PEG, and collagen from, e.g., Kisker Biotechnology (Steinfurt Germany). Other solid phases, such as microtiter plates can also be purchased with, or derivitized to have, covalently bound binding partners (e.g., microtiter plates with bound streptavidin or anti-IgG antibodies from BD Biosciences (Bedford Md.)).

The analyte can be bound to the immobilized binding agent by contacting the solution containing the analyte with the immobilized SBP under conditions in which the analyte is bound to the SBP. For example, microparticles can be added to a presample solution. After attachment of the analyte to the microparticles an analyte-enriched fraction can be prepared by segregating the microparticles using centrifugation, magnetic separation, or filtration, with appropriate washing steps. Removal of unbound contaminants using other solid phases (e.g., microplate wells) can be accomplished by removing the unbound supernatant, and other well known methods.

b. Analyte is Associated with an Ionic Moiety

The analyte can be associated with an ionic moiety using any suitable method, such as those described in previous sections. As indicated above, the analyte can be associated with the ionic moiety before or after binding to the immobilized phase, and can be associated via the binding agent or directly. Thus, binding agents as used herein bind the analyte to an immobilized phase such as a microparticle or substrate. The ionic moiety can be associated with the solid phase first. In this case, the association of the ionic moiety and the analyte is facilitated by binding to the solid phase.

c. Analyte is Released from the Solid or Immobilized Phase

The bound analytes can be released from the microparticles (or other solid phase) using various strategies. For example, an analyte can be displaced using specific agents to compete with the analyte for binding to the immobilized SBP. Alternatively, the analyte can be eluted with non-specific reagents such as denaturing agents (e.g., urea), extreme pH, temperature, high ionic strength buffers, and the like to disrupt the binding. This can be done using changes in buffer, changes in the electric field, pH, addition of an elution buffer, or any method known in the art.

Alternatively, the binding agents having the analyte bound thereto can be freed as a complex by incorporating a cleavable or breakable bond in the linkage between the binding agents and the solid phase (such as the microparticle or substrate). In addition capture agents which are used to capture the analyte during analysis on the microfluidic chip can incorporate a cleavable or breakable linkage between the capturing agents and the capture surface on the microfluidic chip. While the binding agents and capture agents can be the same types of molecules, their roles are different. The capture agent is used when the analyte is captured during analysis (i.e., immobilized in the analysis area). In either case, the bonds include disulfide bridges, diols, restriction enzyme sequences, and bonds that can be dissociated by chemicals or enzymes. For example, the binding agent can be cleaved using proteases or nucleases (e.g., sequence-specific proteases or nucleases). If a linker containing a disulfide bridge is used to anchor the antibodies on the solid phase, the binding complex can be released by using reducing agents such as mercaptoethanol or dithiothreitol. A nucleic acid binding molecule can be cleaved with nucleases.

The following examples are provided for illustration and are not intended to limit the invention.

1. Nucleic Acid Analyte

In one embodiment, the analyte is a nucleic acid. Nucleic acid analytes are themselves poly-ionic, so, while there may be circumstances in which attachment of an additional ionic moiety might be advantageous, it may not be necessary to attach an ionic moiety to mobilize these molecules with electrical field. However, it may be advantageous to initially concentrate the analytes and/or remove contaminants before electrophoresis. This can be done, for example, using nucleic acid binding agents with complementary sequences conjugated to magnetic microparticles. The magnetic microparticles can be added to a sample containing the nucleic acid analyte in the large volume reservoir. After analyte molecules are bound to the microparticles, a magnetic field is applied to gather the microparticles at a specific spot in the large volume reservoir. Contaminants and interfering substances are then removed. Denaturation conditions such as low ionic strength, urea, betaine, high pH or temperature, or a combination of these factors, are used to disrupt the hybridization thereby separating the nucleic acid strands and freeing the bound analytes from the microparticles. Electrophoresis drives the analyte nucleic acids into the second reservoir. Once concentrated in the second reservoir, the nucleic acid analytes are electrophoresed on the microfluidic device to specific capture sites having capture agents that are complementary to the 5' end of the nucleic acid analytes. The nucleic acid analytes bind and can be detected using a labeled nucleic acid detection agent that is complementary to the 3' end of the nucleic acid analytes.

2. Antigen Analyte

In another example, analytes that can act as antigens can be associated with a solid substrate using antibodies as binding agents. Antibodies with affinity to, for example, a protein analyte are conjugated to microparticles. The microparticles are gathered such as by magnetic means (if they are magnetic microparticles) or centrifugal field to a specific spot in the large volume reservoir and the supernatant containing any unbound molecules, contaminants or interfering substances is removed. The protein analytes are freed from the microparticle as a complex. This can be achieved by using cleavable linkers (e.g. as described herein). Appropriate proteases can also be used with optimized reaction conditions to achieve the desired release without undesirable degradation of the analyte. In addition, it is conceivable to engineer specific proteolytic sites in the anchoring components, either the linker or the antibody, for proteases with stringent cleavage site requirements. These proteases can then be used to cleave the binding complex. In one embodiment, an analyte in a blood sample is detected according to the methods of the invention using a preconcentration step in which magnetic microparticles coated with binding agents with affinity to the analyte are added to the blood sample in a large volume reservoir.

VII. Concentrative Electrophoresis of the Analyte

Some or all of the steps of associating the analyte with an ionic moiety (as well as prior sample processing steps) can be carried out in the large volume reservoir. Alternatively, some or all of the steps can be carried out in one or more different vessels and the analyte (and any associated molecules) can be transferred to the large volume reservoir (e.g., by pipetting). As a result, the Analyte-IM Complex will be located in the large volume reservoir.

The large volume reservoir liquid capacity can vary widely. Typical volumes are from about 1 microliter to about 100 mililiters. Preferably, the LVR capacity (and sample volume) is larger than about 5 microliters, even more preferably, larger than about 10 microliters, such as larger than 50 microliters, larger than 100 microliters, and larger than 1 mililiter. In some embodiments, the LVR capacity or sample volume, is between about 1 microliter and 20 milliliters. (It will be appreciated that the sample volume will be less than the LVR capacity, though will usually be at least 25%, more often at least 50%, and often at leat 75% of the LVR volume.) In some embodiments, the sample has a volume of about 10 microliters to about 100 milliliters, more often 25 microliters to 5 mls, even more often 50 microliters to 5 mls or 100 microliters to 25 mls The LVR capacity may be about 50 microliters, 100 µl, 200 µl, 300 µl, 500 µl, 800 µl, 1 milliliter, 2 ml, 3 ml, 4 ml, 5 ml, 6 ml, 10 ml, 20 ml, 30 ml, 40 ml, 50 ml, 60 ml, 70 ml, 80 ml, and 90 ml. In general, a volume that can reasonably be expected to be concentratable by electrophoresis in a reasonable amount of time can be used. This may be determined by the amount of time it takes a charged analyte to move the longest distance in the sample volume.

Figure 3:
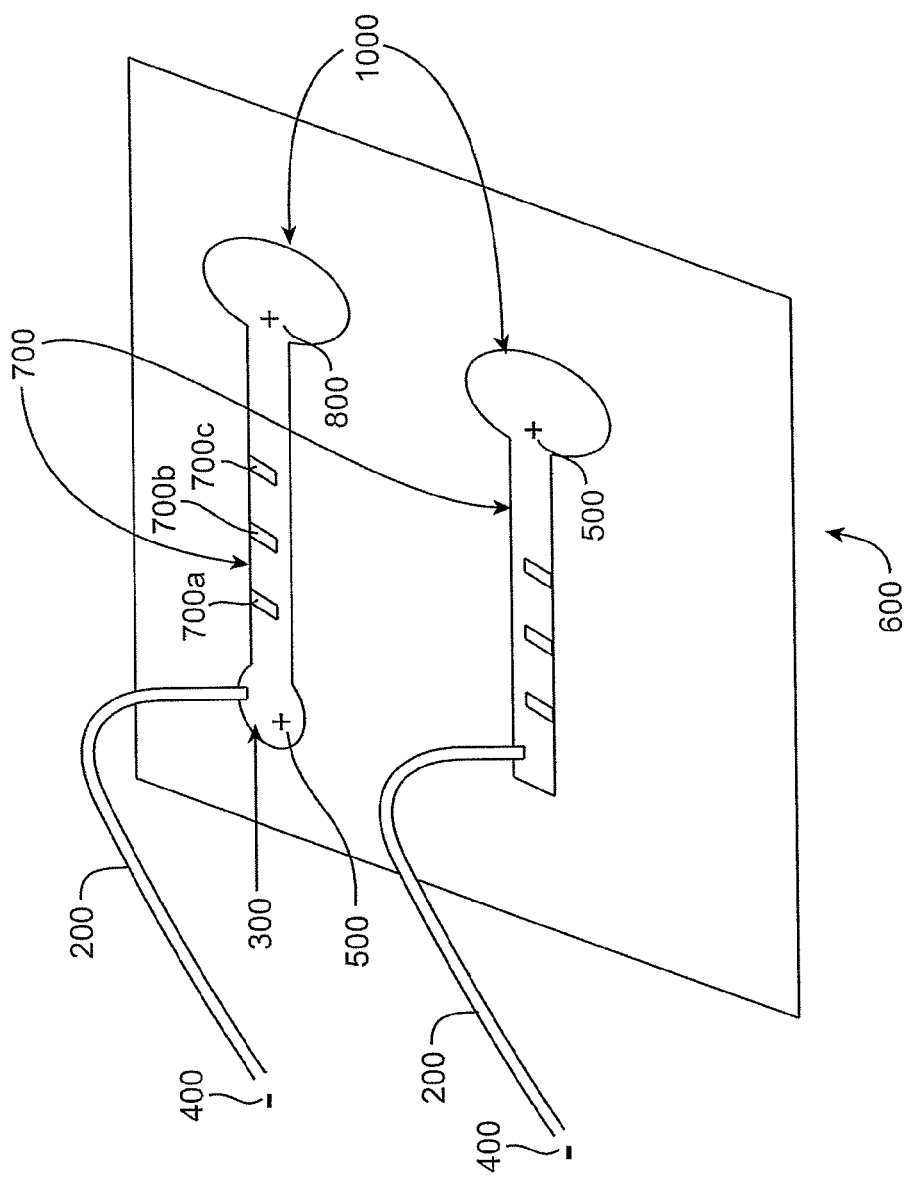
FIG. 3 illustrates a microfluidic device capable of detecting multiple analytes from each of several samples.

Electrophoretic transfer of the charged analyte or the Analyte-IM Complex is accomplished by generating an electric field that extends from the large volume reservoir via the connector to the microfluidic device (e.g., a staging reservoir or analysis area). An exemplary arrangement for the system is illustrated in FIGS. 1-3. The device shown in FIGS. 1 and 3 shows a multiplicity of connectors to connect multiple samples from a multiplicity of large volume reservoirs to the microfluidic device and/or a multiplicity of staging reservoirs.

At least one electrode is placed into, or is integrated into, each large volume reservoir and at least one electrode is placed onto, or integrated into, the microfluidic device. The electric field is applied at a strength such that the analyte will be driven from the large volume reservoirs to the microfluidic device at a selected rate. The position of the electrodes and the electric field applied in the reservoir can be determined to facilitate the best performance for the microfluidic device, for instance to achieve sensitive detection in short time. As an example, the electrodes in the large volume reservoirs can be placed at a point that offers most symmetry and distance in relation to the opening of the connectors which leads to the microfluidic device. This electrode placement is likely to offer a relatively uniform electric field to drive all analytes in the reservoir. The placement of the one or more electrodes in the microfluidic device will depend on the intended operation of the device. The electrode(s) can be placed close to the staging reservoirs if staging reservoirs are desired. It can be placed close to the analysis area if it is desired to drive the analytes to the analysis area directly without using staging reservoirs. Electrodes can also be placed in both places such that electric fields can be applied to drive the analytes sequentially, to the staging reservoirs first then to the analysis area.

The use of a staging reservoir in the microfluidic device allows synchronization and better control the movements of the analytes to the analysis area. The staging reservoir is integral with the chip. The staging reservoir is constructed so as to be in fluidic communication with the analysis area (when any valves in the device interrupting fluid flow are open). The volume of the staging reservoir is smaller than the volume of the large volume reservoir, and is typically less than about 1 microliter, including but not limited to, from about 0.1 pl to about 2 µl, 1 µl to 1 and 10 pl to 0.5 µl, preferably less than 1 microliter, sometimes less than 0.1 microliters, and sometimes less than 1 picoliter.

The connectors shown may be capillary tubes. To facilitate electrophoresis, a connector is filled with conductive media such as a low salt buffer so that an electrical field can be established. When the electric field is applied, the charged analyte (or complex) is transported and driven into the microfluidic device either directly through the analysis area or to a staging reservoir on the microfluidic device to concentrate the analyte before further analysis. The electrical potential of the electrode associated with the large volume reservoir and staging reservoir are selected to achieve the desired rate of transport for the analyte.

The duration of electrophoresis depends on factors such as the concentration and amount of the analyte of interest in the sample, the electrophoretic conditions (current, voltage ionic strength of buffers, etc.), the volume of the initial sample, the charge of the analyte, the sensitivity of the method of detection, and the buffer that is used. Electrophoresis is carried out for a time sufficient to transport an amount of the analyte of interest. When sufficient analyte is transferred, electrophoresis can be discontinued, and if desired, the large volume reservoir and connector can be removed.

In one embodiment, the electrophoresis is carried out until the concentration of analyte in the staging reservoir is at least 2-times the concentration in the large volume reservoir. Sometimes the difference in concentration is at least 3-times, and sometimes at least 5-times, 10-times, 25-times, or 100-times or greater.

More than one large volume reservoir and more than one staging reservoir may be connected to achieve the best configuration for the assay in order to transport the analyte with ease and efficiency. With very large samples, it can be more efficient to use multiple large volume reservoirs in series. In this embodiment LVRs of decreasing volume are connected by connectors in sequence, with electrodes configures so that an analyte is transported serially from one LVR to the next and ultimately to the chip. This allows for voltages to be applied in such a way that analytes can be transferred with speed and minimizing the voltage required to transport analytes into the microfluidic chip. A smaller voltage is advantageous because it reduces any problems with electrolysis, heating and/or gassing in the microfluidic device.

In some embodiments the analyte is transported from a staging reservoirs to one or more intermediate reservoirs prior to transport to the analysis area. This allows multiple assays (e.g., assays carried out in different solutions or with incompatible reagents) to be easily carried out. For example, the contents of a staging reservoir can be divided and one portion used for nucleic acid detection and the other for protein detection. Using intermediate reservoirs may also allow use of a larger volume of sample.

VIII. Transport of Analyte, Charged Analyte, or Analyte-IM Complex to the Analysis Area For detection and analysis of the analyte, the analyte (which may be associated with an ionic moiety and/or part of an analyte complex) is transported from the large volume reservoir or staging reservoir to the analysis area of the device. In preferred embodiments the analysis area comprises multiple capture agents (which may be the same or different, and which may or may not be arranged in an ordered array) that bind the analyte or analyte-IM complex (and may bind the carrier molecule, ionic moiety, or other component of the complex).

Once the analyte and/or the complex comprising the analyte has been electrophoresed from the LVR to the microfluidic chip, the analyte/complex can be transported to the capture site using any means known in the art, for example micropumps, capillary action, and/or electrophoresis. In a preferred embodiment, electrophoresis is used. It will be appreciated that electrophoresis out of the staging reservoir across the array will require that an electric field formed between the electrode in the staging reservoir and the electrode in or near the analysis area. Alternatively, if no staging reservoir is used, the electric field is formed between the electrode in the LVR and the electrode in or near the analysis area.

IX. Analysis Area and Detection of Analyte

Analyte can be detected, quantified or analyzed in the analysis area of the chip. In one embodiment, the analysis is done without immobilizing the analyte in the analysis area (e.g., using light scattering, flow cytometry, or fluorescent detection or other detection methods carried out in solution). For example, the analytes can be labeled with fluorophores and analyzed in the analysis area with apparatus commonly use in flow cytometers to analyze fluorescent entities by exciting the fluorophores with laser of appropriate wavelength and measure the emitted fluorescent light. It will be appreciated that, consistent with the design of most microfluidic devices, the analysis area is usually a channel or chamber of the chip.

Alternatively, detection involves binding of the analyte by an immobilized capture agent in the analysis area. A capture agent is a molecule that can capture an analyte or analyte complex by specifically binding the analyte or a member of the complex. Members of the complex that can be bound by the capture agent include the analyte, the carrier molecule, the carrier molecule/analyte complex, an ionic moiety, a second antibody (if used) and a label. Thus, the capture agent can be, for example, one or more antibodies, nucleic acids, receptors, and/or ligands.

The capture agent can be immobilized to the microfluidic device at a capture site using any methods known in the art. For example, one or more antibody capture agents can be attached via the Fc portion of the antibody. The capture agent can be attached to the capture site by covalent or non-covalent attachment, but, preferably, the attachment is strong enough that the movement of liquid over the capture site will not detach the capture agents. The various reagents and reaction conditions used are known in the art (see, e.g., "Chemical Modification of Proteins" by Gary E. Means and Robert E. Feeney, "Bioconjugate Techniques" by Greg T. Hermanson and "Chemical Reagents for Protein Modification" by Roger L. Lundblad). Exemplary methods of attachment of capture agents to capture sites on solid phase substrates can be found for example in U.S. Pat. Nos. 5,629,213, 5,688,642, 5,585,275, and International Patent Application WO9745730.

Once attached at the capture site, the capture agents can capture the analyte or a member of the analyte complex as it is moved over the capture site. The capture agent and analyte or analyte complex typically bind by a noncovalent interaction, but covalent binding may be used. For nucleic acid analytes or nucleic acid ionic moieties, capture agents can be, for example, complementary nucleic acids. For protein analytes, capture agents can include antibodies, ligands, lectins and receptors specific for the protein analyte. Carbohydrate and lipid analytes can be captured using antibody capture agents. Antibody carrier molecules can be captured using antibodies, antigens or other molecules that specifically bind antibodies. For example, if the carrier molecule is a human antibody, the capture agent can be a goat anti-human antibody.

The conditions for capture can be manipulated to allow specific capture of a targeted member of the analyte complex. Conditions such as the buffer, the rate of movement over the capture site, the temperature and the capture time can be chosen to allow binding of only a specific analyte or to also bind to variants such as nucleic acids with single base changes or variant proteins. Alternatively, the capture agent can be chosen to bind only a specific analyte or to variants.

The capture agents can be directed to a specific location or capture site on a microfluidic device by any method known to one of skill in the art. For example, the capture agents can be directed and associated to a specific capture site using pumping devices, or photolithography and photoreactive reagents.

Often analyte is detected based on a signal from a detectable label. A label refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable physical signal, molecule or complex. Detectable labels suitable for use in the present invention include any composition detectable by spectroscopic, photochemical, biochemical, immunochemical, electrical, optical, chemical or physical means and the like. A detectable lablel, when used, can be added to any component of the final complex which may be bound to the capture agent. For example, the label can be bound to a carrier molecule, an analyte, an ionic moiety, or a binding agent. Detectors (e.g., flurosecnce readers, spectrophotometers, etc.) for use in a microfluidic environment are well known in the art.

Figure 7:
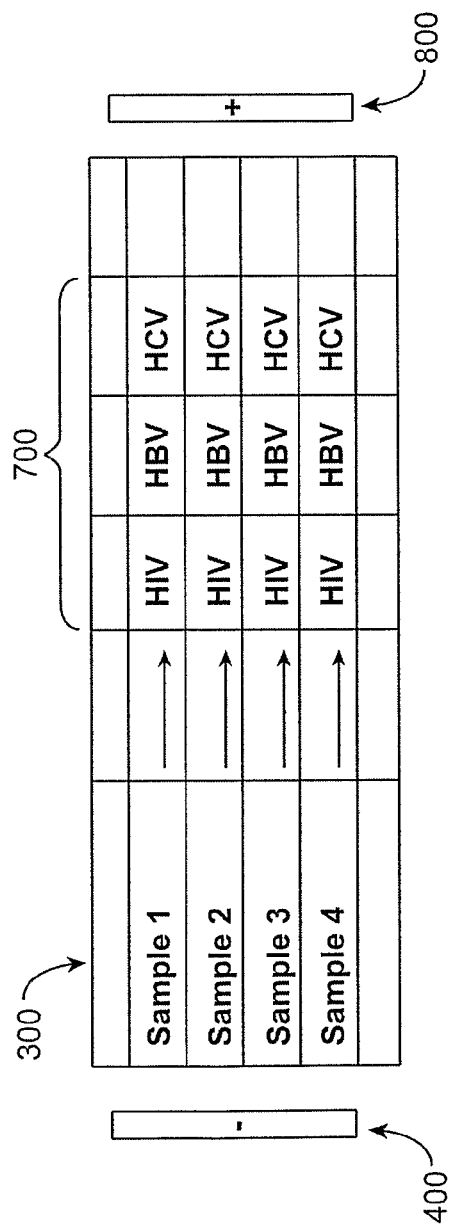
FIG. 7 shows a diagram of an exemplary assay format for detection of viral nucleic acids or proteins in a blood sample. Analytes in multiple samples are transported (e.g., by electrophoresis) over multiple detection sites in the analysis areas.

It will be appreciated that multiple analytes can be detected in the same sample. For example, as illustrated in FIGS. 3 and 7, specified regions of the analysis area can be associated with capture moieties specific for particular analytes.

X. Specificity of the Assay

The specificity of the assay can be provided at any one or more of the steps in the methods described herein. For example, one or more steps can involve binding to general classes of molecules and one or more steps can require specific binding to only the analyte of interest. When specificity is desired, a specific ionically-modified antibody can be used, a specific carrier molecule can be used, a specific binding agent can be used, a specific detection molecule can be used, and/or a specific capture agent can be used on the microfluidic device. Thus, for example, initially the analyte in the sample can be concentrated using microparticles coated with specific binding molecules. Alternatively, the microparticles can be coated with binding molecules that bind a general class of molecules that includes the analyte. Classes of general molecules includes: phosphorylated proteins, glycoproteins, nucleic acids, antibodies, lipids, sugars, shared receptor domains, shared motifs, conservative nucleic acid or amino acid motifs, shared carriers, and shared epitopes.

XI. Antibodies Used in the Assay

It will be appreciated by the reader that antibodies may play several roles in the method of the invention. For example, an antibody can also be the analyte, as described in the Example below. The term "antibody" is refers to immunoglobulins comprising two heavy and two light chains, and antigen binding fragments thereof (including Fab, Fab' F(ab')2, Fabc, and Fv). Fragments may be produced by recombinant DNA techniques, or by enzymatic or chemical separation of intact immunoglobulins. The term "antibody" also includes one or more immunoglobulin chains or fragments that are chemically conjugated to, or expressed as, fusion proteins with other proteins, single chain antibodies, and bispecific antibodies. See, e.g., Harlow & Lane, Antibodies, A Laboratory Manual, Cold Spring Harbor Press, New York (1988); Current Protocols in Immunology (J. E. Coligan et al., eds., 1999, including supplements through 2005); Songsivilai & Lachmann, Clin. Exp. Immunol. 79:315-321 (1990); Kostelny et al., J. Immunol. 148, 1547-1553 (1992). Antibodies can be monoclonal or polyclonal. However, in some embodiments, monoclonal antibodies are used to ensure binding to a specific epitope on the protein.

In some embodiments, two or more antibodies are bound to the analyte (or other analyte-IM complex component) concurrently at some point in the assay. Under such conditions, the antibodies either bind different epitopes on the analyte, a second antibody binds to a first antibody, or a second antibody binds to the antibody/analyte complex. In other embodiments, a first antibody can be removed prior to addition of a second antibody.

Depending on the function they serve, antibodies can be ionically-labeled and/or be modified to include a detectable label for subsequent detection. As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical, chemical or physical means and the like.

XII. Apparatus and System

The invention provides an apparatus and system for carrying out the methods described herein. In one embodiment the microfluidic device has a staging reservoir in fluidic communication with an analysis area that comprises capture agents that bind the (i) the analyte, (ii) an antibody or (iii) a nucleic acid (i.e., carrier molecules or elements of the analyte-IM complex). As noted above, the analysis area is typically a region of a microfluidic channel and the capture agents are immobilized on at least on surface of the channel. The sample reservoir has a fluid capacity as described above (e.g., 0.1 pl to about 2 µl). The device further comprised a first microelectrode associated with the staging reservoir and a second microelectrode associarted with the analysis area. The electrodes are positioned such that application of positive charge to one electrode and a negative charge to the other electrode results in an electric field sufficient for electrophoresis of a charged molecule from the staging reservoir to the analysis area. Thus, one electrode may be situated in the staging reservoir and the second is situated in the analysis area distal to (relative to the staging reservoir) the immobilized capture agents.

In one embodiment, the device comprises multiple units of staging reservoir and analysis area, as described above. Each combination of staging reservoir and analysis area can be referred to as an "operational unit."

In one embodiment, at least one analysis area of the device comprises capture agents that bind molecules from more than one pathogenic organism. In an embodiment, at least one, and optionally all of the pathogenic organisms, are viruses. In an embodiment, at least one, and optionally all of the pathogenic organisms, are bacteria. In one embodiment, molecules from pathogenic organisms are nucleic acids, proteins, or toxins.

In a related embodiment the invention provides a system that comprises a microfluidic device of the invention and further comprises a large volume reservoir and/or connector and/or source of electric current and/or a computer-implemented control system can be used to activate or switch polarity of the electrodes (400, 500) as needed for concentration, transport and/or analysis. The system uses electrophoresis to concentrate a charged analyte and to introduce or apply the sample to a microfluidic device. Electrophoresis is used to move and concentrate a charged analyte from a large volume reservoir into a staging reservoir on or in a microfluidic device. A general arrangement for the system or apparatus is illustrated in FIGS. 1 and 2. The system generally includes a microfluidic device 600, at least one large volume reservoir 100, at least one staging reservoir 300, a connector 200, and at least two electrodes 400 and 500 (or 800) for electrophoresis. In one embodiment, the microfluidic device also includes an effluent well for collection of any effluent left over from the sample analysis (e.g., see FIG. 3).

Multiple connectors 200 between large volume reservoirs 100 and staging reservoirs 300 are shown in FIG. 1 using capillary tubing. The capillaries 200 are filled with fluid, such as low salt buffers that serve the purpose of connecting the electrodes (400 and 500) to form an electrical field. This allows a charged analyte to be electrophoresed from a large volume reservoir 100 to a staging reservoir 300 (see FIG. 3).

The electrodes 400 and 500 can be connected to the reservoirs (100, 300) and/or microfluidic device 600 using any means known in the art to produce an appropriate electric field. It is understood that the materials, samples, buffers, and manufacture of all of the components are provided to be compatible for the electrophoresis of materials. The electrodes (400, 500) are operably attached to the reservoirs (100, 300). Operably attached means that the electrode is positioned in or near the reservoir so that application of a voltage or potential generates an electric field through which charged molecules are transported. In one embodiment, the electrode is embedded in the material of the reservoir or device (e.g., contained in the substrate). Further, when more than two electrodes (400, 500) are present, a computer-implemented control system can be used to switch polarity of the electrodes (400, 500) as needed for concentration, transport and/or analysis. The control system can be configured to be responsive to a detector that measures the presence and/or position of analyte in the analysis area.

In one embodiment, the system comprises a multiplicity of operational units each in fluidic communication with a different large volume reservoir. In one embodiment, the system comprises a multiplicity of operational units, each with a staging reservoir and associated electrode, and a control system that applies a charge of the same magnitude and duration to each of the electrodes.

Instrumentation known in the art can be used for applying voltage, controlling fluid transport, flow rate and direction within the device, detection instrumentation for detecting or sensing the analyte of interest, processors, e.g. computers for instruction the controlling instrumentation, receiving data from the detectors, and for analyzing storing and interpreting the data, and providing the data and interpretations in a readily accessible reporting format.

XIII. Exemplary Embodiments

Exemplary embodiments of the methods will now be described with reference to FIGS. 4-6.

Figure 4:
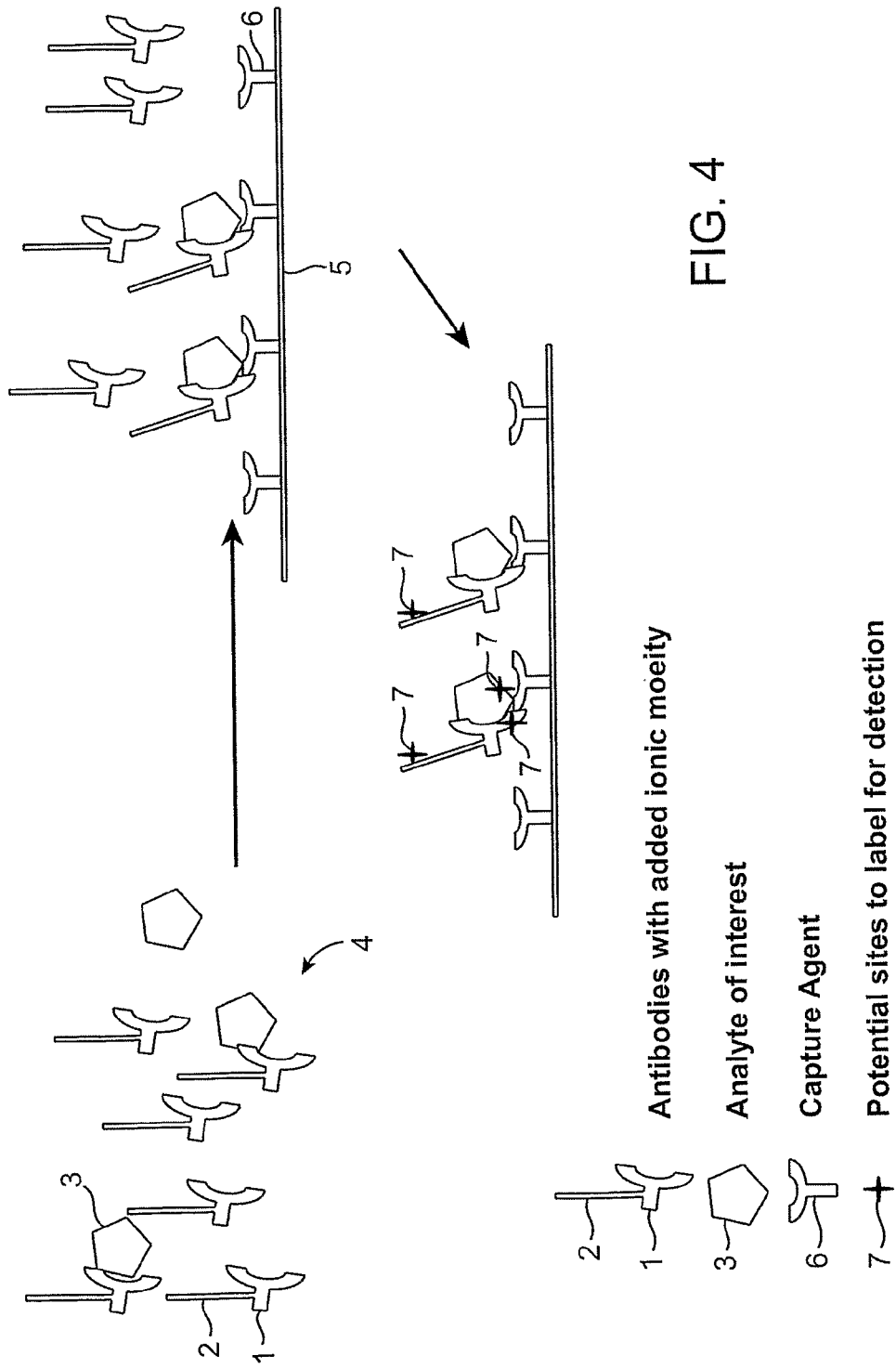
FIG. 4 is a diagram illustrating an embodiment of the invention in which an antibody tagged with an ionic moiety binds to an analyte of interest in a large volume reservoir (LVR) and forms a complex, and the complex is electrophoresed onto a microfluidic device. The microfluidic device has a capture agent (a second antibody specific for the analyte of interest but recognizing a different epitope) attached thereto.

In the embodiment illustrated in FIG. 4, an ionically-labeled antibody carrier molecule is used to confer ionic properties on the analyte. A first antibody 1 with an ionic moiety 2 attached, specifically binds to the analyte 3 in the sample in a large volume reservoir producing an antibody/analyte complex 4. The ionically labeled antibodies and complexes are transported electrophoretically to a staging reservoir. The complexes are then transported to an analysis area having a substrate 5 having capture agents 6 bound. The capture agents 6 are second antibodies specific to analyte 3. The capture agent antibodies 6 bind to an epitope of analyte 3 different from that of the first antibody 1, or can specifically bind to the antibody/analyte complex 4, but do not bind to any free first antibodies 1. A detectable label can be attached directly to any of the molecules (potential sites 7) at any point before or after capture of the analyte 3. In other embodiments, the analyte/ IM complex bound to a capture agent is detected using a labeled third antibody that binds to a different site on the analyte 3 or to the antibody/analyte (4) complex.

The specificity of the assay can be conferred by the specificity of first antibody 1, the specificity of capture agent 6, or both. Other embodiments can include an analyte-specific detection label used in combination with a capture agent 6 that binds to the first antibody 1 or to the ionic moiety 2.

In the embodiment illustrated in FIG. 5, analyte 3 is associated with a charge by binding to magnetic microparticles 8 in the large volume reservoir. In this embodiment, microparticles 8 are coated with an antibody binding agent 11. These are added to the sample in an appropriate buffer to allow the analytes 3 to bind to the antibody binding agents 11. If desired, interfering, contaminating and/or unwanted substances are removed after magnetically concentrating the microparticles 8 to a specific area of the reservoir. Additional steps can be performed to further reduce unwanted substances. A second antibody 1 having an ionic moiety 2 attached, is added to the antibody/analyte complex in the large volume reservoir. The second antibody 1 binds possibly via a different epitope on the analyte 3. Optionally the order of addition of antibody 1 vs. the microparticles coated with an antibody binding agent 11 can be reversed. After the bound analyte/antibody complex (3/11/1/2) is formed, any excess antibody 1, interfering, contaminating and/or unwanted substances are removed after magnetically concentrating the microparticles 8 to a specific area of the reservoir. Additional wash steps can be performed to further reduce unwanted substances. The bound analyte/antibody complex (3/11/1/2) is then removed from the microparticle 8 using an appropriate cleaving agent. This complex (3/11/1/2) is then electrophoresed to concentrate the analyte 3 into a staging reservoir. After concentration, the complex is electrophoresed over the capture site 5 of the microfluidic device. In this embodiment, the capture agents 6 attached to the capture site 5 specifically bind to the ionic moiety 2 (for example, if the ionic moiety 2 is a nucleic acid molecule, the capture agent 6 is a complementary nucleic acid molecule). A detectable label 7 can be attached to any of the molecules involved, including the analyte 3; the antibody binding molecule 11 on the microparticle 8, the second antibody 1, or the ionic moiety 2. The specificity in this reaction can be provided at any step, including binding to the binding agent 11 on the microparticle 8, binding of the second antibody 1 or both. In an embodiment, the capture agent 6 can be a third antibody that binds to a different epitope on the analyte 3 or that binds to the antibody/analyte (1/3 or 11/3) complex specifically and does not bind to free antibody (1 or 11).

Figure 6:
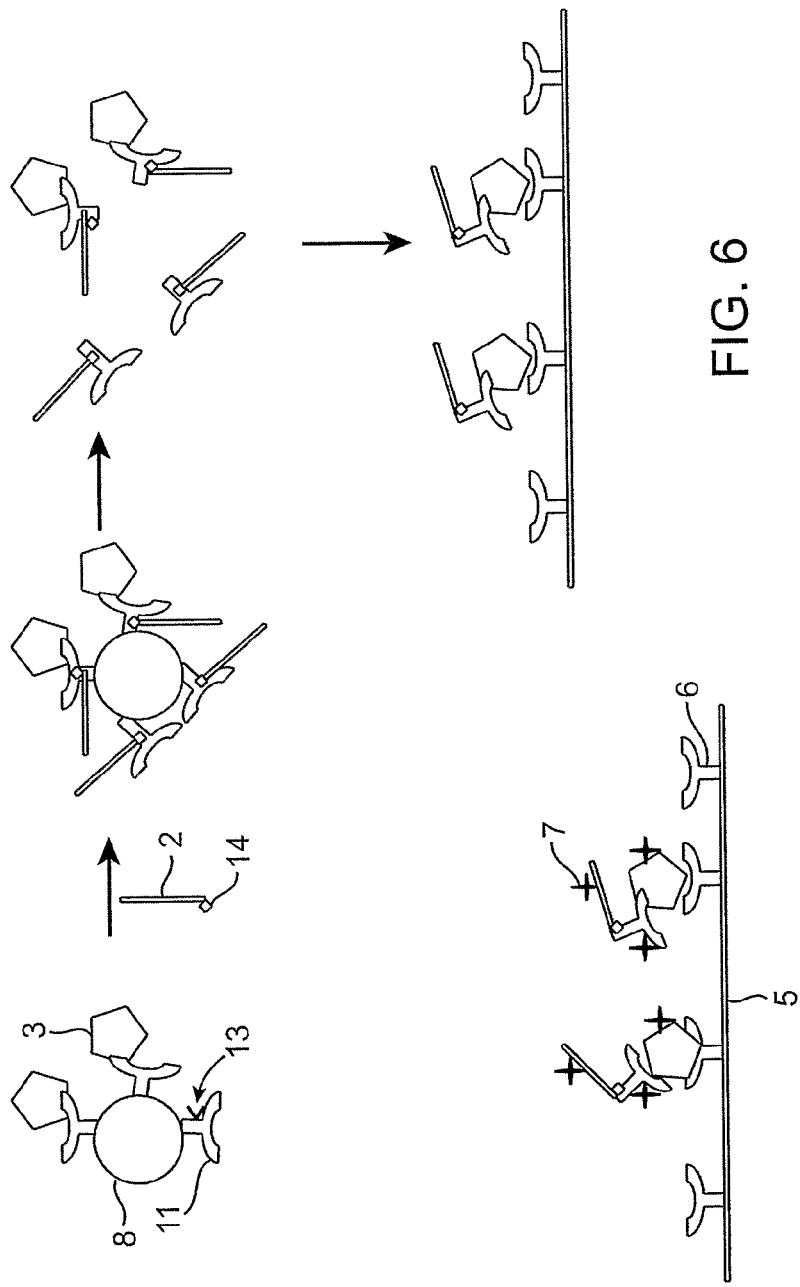
FIG. 6 illustrates an embodiment similar to that illustrated in FIG. 5, in which the analyte of interest is initially bound to microparticles. An ionic moiety is attached to the microparticle-bound antibody using a biotin/avidin type linkage. The antibody is cleaved to release the analyte from the microparticle and introduced to the microfluidic device by electrophoresis. The complex is captured on the microfluidic device using a second antibody specific for the analyte.

The embodiment illustrated in FIG. 6 is similar to that of FIG. 5, and involves attachment of an ionic moiety 2 later in the process and can be used in cases when the ionic moiety 2 may interfere with an earlier binding or purification step. In this embodiment, an avidin/biotin pair (13/14), or similar specific binding pair, is used to attach the ionic moiety 2 to the antibody 11 as a tag/binding agent pair. The analyte 3 is first immobilized onto magnetic microparticles 8 coated with specific binding agents 11. In the illustration of FIG. 6, the binding agents are antibodies 11 that specifically bind to the analyte 3, modified with a biotin tag 13. The ionic moiety 2 conjugated to avidin (or binding agent to the tag) is mixed with the microparticles 8 and binds to the antibody binding agent 11 via the avidin/biotin bond 13/14. At any point in the process, the magnetic microparticles 8 can be concentrated to a specific area in the large volume reservoir by applying a magnetic field to allow washes, buffer changes, and/or removal of the analyte 3 from the microparticles.

Prior to electrophoresis to concentrate the analyte 3 into the staging reservoir, the antibody binding agents 11 are cleaved from the microparticles 8, for example by addition of a specific protease. The analyte 3/antibody 11 complex and any other charged molecules in the sample are then concentrated into the staging reservoir using electrophoresis. After concentration, the complex is moved over a capture site 5. The analyte 3 is captured by specific capture agents 6 on the capture site 5. In this embodiment, the capture site 4 is coated with antibody capture agents 6 that specifically bind to the analyte 3 at a different epitope from that recognized by the first antibody 11. A detection label 7 can be bound to any of the components, including the antibody binding agent 11, the analyte 3, or the ionic moiety 2.

Table 3 provides examples, for illustration and not limitation, of combinations of analytes, ionic moieties, carrier molecules, and capture agents that may be used in the methods of the invention.

TABLE 3

Examples of analyte/ionic moiety/carrier molecule/capture agent combinations

|  | Analyte | Ionic moiety | carrier molecule | binding agent | capture agent |
|---|---|---|---|---|---|
| See Nucleic Acid. embodiment | polypeptide | nucleic acid | antibody | antibody | antibody |
|  | nucleic acid | (analyte) | none or nucleic acid | comp. nucleic acid | comp. nucleic acid |
|  | antibody | poly-lysine | none or second antibody | antigen | antigen |
|  | carbohydrate | nucleic acid | antibody | lectin | antibody |

EXAMPLES

This is a generic description for a biochip used for infectious disease detection. The chip contains electrodes, sample wells, specific detection areas, channels and valves. Multiple samples can be loaded and driven through the detection areas for identification and quantification using electrophoresis. The different samples can be loaded concurrently or sequentially and loading can be controlled with microfluidic valves. The common reagents used in detection can be introduced through the channels in the device.

Example 1

HIV/HBV/HCV Test

FIG. 3 illustrates a microfluidic device 600 for detecting the presence of HIV, HBV, and/or HCV antigens (protein analytes) in a sample. The microfluidic device has electrodes 500 and 800 for use, along with LVR electrode 400, in electrophoresis. A biological sample suspected of containing HIV, HBV or HCV is introduced into the large volume reservoir (not shown) and mixed with antibodies specific to HIV, HCV, and HBV protein analytes. The antibodies have an ionic moiety attached. Antibody/analyte complexes are allowed to form and, the complexes are electrophoresed over the capture sites (700a, 700b and 700c) in the Analysis area 700 (optionally after concentration in staging reservoir 300). Reagents and unbound molecules flow into eluent chamber 1000, and may be removed. The HIV capture site 700a has antibody capture agents specific to an HIV protein analyte. The HBV capture site 700b has antibody capture agents specific to an HBV protein analyte and the HCV capture site 700c has antibody capture agents specific to an HCV protein analyte. The presence of HIV, HBV, and/or HCV can be identified by a signal from a detectable label at the specific capture site (700a, 700b or 700c) for that viral analyte. FIG. 3 illustrates embodiments in which analyte is transported electrophoretically from the large volume reservoir to the analysis area via a staging reservoir (top) or without a staging area (bottom).

FIG. 7 is a schematic representation of a chip that illustrates an embodiment of the assay with reference to a blood test for infectious viruses such as HIV, HBV and HCV. The current limit of sensitivity for FDA approved clinical tests for HIV is about 50 viral copies per ml for Roche's UltraSensitive AMPLICOR HIV-1 MONITOR® Test, v1.5 using PCR technology or Bayer's Versant HIV 3.0 using b-DNA technology. This means that for a typical sample, the full 1 ml sample is needed to provide enough viral RNA for detection. It is impractical to load the entire 1 ml of sample solution into or onto the chip. Even using preparatory steps to concentrate the sample, such as centrifugation, ethanol precipitation, or capturing the target RNA with microparticles followed with elution, the ending sample volume will be in the range of tens or hundreds of microliters (μls). Since the testing areas in microfluidic chips usually range from a few to several hundred microns, the volume that can be handled even by a large chip will be in the range of a few nanoliters (nls). A significant time would be needed to move an entire prepared sample solution into the chip through the detection area and to allow sufficient time for the analytes to contact the detection agents in a specific analysis area to bind. This then results in an unacceptably high turnaround time to yield test data. For this reason, current practice using chip-for-detection typically uses the products of PCR reactions which has high concentrations of analytes for application to a chip.

However, using the methods and apparatus disclosed herein, electrophoresis can transport the viral RNA or DNA from a large sample into the analysis area of a chip with the option of passing through a staging reservoir resulting in concentration of the sample to a level that can be used for detection on the chip. FIG. 7 shows a diagram of an exemplary assay format for detection of viral nucleic acids or proteins in a blood sample. FIG. 7 depicts a chip 600 that allows the transport of analytes in multiple samples (located in staging reservoirs 300) by electrophoresis with electric field applied in the direction of the arrows between the electrodes (400, 800) over multiple detection sites 700 in the analysis areas. The detection sites 700 are labeled as "HW," "HBV," and "HCV" to indicate the presense of capture agents specific for proteins or nucleic acids from these viruses, or to binding moieties, etc. specifically associated with one of the viruses. In this example, four samples are being tested simultaneously. In an alternative embodiment analyte is transported from the staging reservoir other than electrophoretically (e.g., using peristaltic pumps).

Example 2

HIV/HBV/HCV Test for Viral Nucleic Acid Analytes

To detect viral nucleic acid analytes in patient samples, ionic or nonionic detergent is added to the patient sample to disrupt the viral coating and expose the nucleic acids in the large volume reservoir. If nonionic detergent is used and the samples have a low ion content, electrophoresis can be used to drive the viral nucleic acids directly into the analysis area 700. Alternatively, the viral nucleic acids are driven by electrophoresis to the staging reservoir 300 first. Subsequently, these viral nucleic acids are delivered from the staging reservoir to the analysis area 700 by electrophoresis or other means such as micropumps.

If ionic detergents are used, further sample preparation is used as follows. Magnetic microparticles conjugated with complementary nucleic acids or analogs (binding agents) are added to the sample containing the viral RNA or DNA analyte. The viral RNA or DNA binds to the binding agents on the microparticles. After wash steps to remove excess detergents, the viral nucleic acids are dissociated from the microparticles using a denaturing agent such as urea or heat. Then the viral nucleic acids are delivered to the analysis area 700 or concentrated into the staging reservoir 300 using electrophoresis.

After concentration into the staging reservoir 300, electrophoresis is then used to pass the nucleic acid analytes over specific capture sites (700a, 700b and 700c) on the microfluidic device 600 at a specific location. The capture agents are nucleic acids or their analogs with sequences complementary to the specific viral nucleic acid analytes. Nucleic acid analytes bind at the specific detection area for the virus and are detected by applying labels made of nucleic acids or their analogues with sequences complementary to a section of viral sequences other than that used for capturing. The nucleic acid detection agents are conjugated with detectable entities such as fluorescent dyes or enzymes, which can be detected by fluorescence or chemiluminescent substrates. A sample is identified as containing the specific virus when a label is detected in the specific area of the microfluidic device (700a, 700b or 700c).

Example 3

HIV/HBV/HCV Test for Antibody Analytes

An example to detect antibodies against HIV, HBV or HCV viral antigens in the patient samples is performed as follows:

A specific viral antigen as binding agent for each antibody is conjugated to magnetic microparticles via a cleavable bond such as a double stranded DNA with a restriction site Alternatively, anti-human Fc antibodies modified with ionic moieties can be used. The microparticles are mixed with blood samples from human patients in a large volume reservoir to capture any antibodies for specific viral antigens. After wash steps to reduce unwanted impurities, the complex is freed from the microparticles by cleaving with a restriction enzyme. The complex is then driven by electrophoresis into a staging reservoir. After concentration into the staging reservoir, the complex is driven to analysis sites (700*a*, 700*b*, 700*c*). As an example, to detect the complexes, capture agents with specific affinity to one of the entities in the complex are conjugated on the chip surface at each specific site (700*a*, 700*b*, and 700*c*) to recapture the complexes and, thus, to identify the presence of antibodies against specific viral antigens in the sample. For instance, if viral antigens are used as the binding agent on magnetic beads in the sample preparation step, the capture agent can be a specific anti human antibody. Conversely, if the specific anti-human antibody is used first as binding agent, viral antigen can be used to recapture the complex of the patient antibody and the anti-human antibody. The recaptured complexes are detected by labeling agents that have affinity to the complex. Agents with affinities to the complex can be a different antibodies against the human antibodies or the viral antigen whichever is appropriate. They can be labeled with fluorescent dyes or enzymes such as horseradish peroxidase or alkaline phosphatase. Alternatively, the first binding agent can be modified to carry both ionic moieties and tags or specific complementary sequences for detection. For instance, oligonucleotide ionic moieties can be conjugated to the first binding agent to provide ionic charges and a sequence for binding by a labeled oligonucleotide complementary to it. Alternatively, the first binding agent can be biotinylated or tagged with entities such as poly-histidine and detected by avidin or anti-poly histidine antibody conjugated with labels.

Example 4

HIV/HBV/HCV Test for Mixed Analytes

The methods can be used to detect mixed analytes from various sources, for example proteins from one source and nucleic acids from a different source. This test detects a nucleic acid coding for HIV tat, an HBV capsid protein, and an antibody against a specific HCV antigen on the same microfluidic device or even in the same patient sample. The capture agents provided at the capture site include a nucleic acid complementary to the HIV nucleic acid in one capture site 700*a*, an antibody that specifically binds the HBV capsid protein in a second capture site 700*b*, and a HCV antigen as capture agent that specifically binds an antibody against this antigen in a third capture site 700*c*. Alternatively, the methods can be used to detect multiple analytes from the same source (e.g., pathogen-specific antigen, pathogen specific DNA and pathogen specific antibodies) from a patient sample.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated by reference. Citation of publications and patent documents is not intended as an admission that any such document is pertinent prior art, nor does it constitute any admission as to the contents or date of publication of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for introducing an analyte of interest in a sample to a microfluidic device, comprising:
providing an aqueous sample in a large volume reservoir comprising a first microelectrode operably attached thereto, said sample containing the analyte and having a volume of greater than or equal to 1 microliter, wherein the analyte of interest is charged or has been associated with a charged molecule;
electrophoresing the analyte via a connector from the large volume reservoir to a staging reservoir positioned in a microfluidic device, wherein the connector fluidically connects the large volume reservoir and the staging reservoir, and wherein the microfluidic device comprises an analysis area, a second microelectrode located in the staging reservoir and a third microelectrode located in or distal to at least a portion of the analysis area, said microelectrodes being configured such that an electric field may be generated between the electrodes and a charged analyte electrophoresed from the first microelectrode to the second microelectrode and from the second microelectrode to the third microelectrode; and
transporting the analyte to the analysis area for a time sufficient to result in a higher concentration of analyte in the analysis area than in the sample.

2. The method of claim 1, wherein the aqueous sample in the large volume reservoir has a volume which is about 100 to about 1000 times greater than the volume of the staging reservoir.

3. The method of claim 1, wherein said sample has a volume of from 1 microliter to 100 milliners.

4. The method of claim 3, wherein said sample has a volume of from 1 microliter to 20 mililiters.

5. The method of claim 1, wherein the aqueous sample in the large volume reservoir has a volume which is about 5 to about 1000 times greater than the volume of the staging reservoir.

6. A method for introducing an analyte of interest to a microfluidic device, comprising:
introducing a solid phase hound analyte into a large volume reservoir to provide a sample, said sample having a volume of greater than or equal to 1 microliter, wherein the analyte is charged or has been associated with a charged molecule;
exposing the solid phase-bound analyte to conditions sufficient to free the analyte from the solid phase;
electrophoresing the analyte from the large volume reservoir to a microfluidic device via a connector, wherein the microfluidic device comprises an analysis area, and the large volume reservoir and the microfluidic device are fluidically connected via the connector; and
transporting the analyte to the analysis area for a time sufficient to result in a higher concentration of analyte in the analysis area than in the sample, wherein the analyte is continuously flowed from the large volume reservoir to the analysis area during said time.

7. The method of claim 6, wherein said sample has a volume of from 1 microliter to 100 mililiters.

8. The method of claim 7, wherein said sample has volume of from 1 microliter to 20 mililiters.

9. The method of claim 6, wherein the solid phase is a microparticle.

10. The method of claim 9, wherein said microparticle is a magnetic microparticle.

11. A method for introducing an analyte of interest in a sample to a microfluidic device, comprising:
    providing an aqueous sample in a large volume reservoir, said sample containing the analyte and having a volume of greater than or equal to 1 microliter, wherein the analyte is charged or has been associated with a charged molecule;
    electrophoresing the analyte from the large volume reservoir to a microfluidic device via a connector, wherein the microfluidic device comprises an analyis area, and the large volume reservoir and the microfluidic device are fluidically connected via the connector; and
    continuously flowing the analyte to the analysis area for a time sufficient to result in a higher concentration of the analyte in the analysis area than in the sample, wherein the large volume reservoir is a chamber that is not integral with said microfluidic device.

12. The method of claim 11, wherein said sample has a volume of from 1 microliter to 100 milliliters.

13. The method of claim 12, wherein said sample has a volume of from 1 microliter to 20 milliners.

14. The method of claim 11, further comprising providing at least one other aqueous sample in a large volume reservoir fluidically connected to the microfluidic device, the microfluidic device further comprising at least one other analysis area for said one other sample.

15. The method of claim 11, wherein said connector is a capillary tube.

16. A method for introducing an analyte of interest in a sample to a microfluidic device, comprising:
    providing an aqueous sample in a large volume reservoir, said sample containing the analyte and having a volume of greater than or equal to 1 microliter, wherein the analyte is charged or has been associated with a charged molecule;
    electrophoresing the analyte from the large volume reservoir to a microfluidic device via a connector, wherein the microfluidic device comprises an analyis area, and the large volume reservoir and the microfluidic device are fluidically connected via the connector; and
    continuously flowing the analyte to the analysis area for a time sufficient to result in a higher concentration of the analyte in the analysis area than in the sample, wherein said large volume reservoir is a well of a microwell plate, an eppendorf tube, or a test tube.

17. The method of claim 16, wherein said sample has a volume of from 1 microliter to 100 mililiters.

18. The method of claim 17, wherein said sample has a volume of from 1 microliter to 20 mililiters.

19. The method of claim 16, further comprising providing at least one other aqueous sample in a large volume reservoir fluidically connected to the microfluidic device, the microfluidic device further comprising at least one other analysis area for said one other sample.

20. The method of claim 16, wherein said connector is a capillary tube.

21. A method for introducing an analyte of interest in a sample to a microfluidic device, comprising:
    providing an aqueous sample in a large volume reservoir, said sample containing the analyte and having a volume of greater than or equal to 1 microliter, wherein said analyte is covalently bound to an ionic moiety or is associated with a charged molecule by being bound to a carrier molecule that is ionically charged or is modified to be ionically charged;
    electrophoresing the analyte from the large volume reservoir to a microfluidic device via a connector, wherein the microfluidic device comprises an analyis area, and the large volume reservoir and the microfluidic device are fluidically connected via the connector; and
    continuously flowing the analyte to the analysis area for a time sufficient to result in a higher concentration of the analyte in the analysis area than in the sample.

22. The method of claim 21, wherein the carrier molecule is selected from the group consisting of an antibody, a receptor, a ligand, and an antigen.

23. The method of claim 21, wherein said sample has a volume of from 1 microliter to 100 mililiters.

24. The method of claim 23, wherein said sample has a volume of from 1 microliter to 20 mililiters.

25. The method of claim 21, further comprising providing at least one other aqueous sample in a large volume reservoir fluidically connected to the microfluidic device, the microfluidic device further comprising at least one other analysis area for said one other sample.

26. The method of claim 21, wherein said connector is a capillary tube.

27. A method for introducing an analyte of interest in a sample to a microfluidic device, comprising:
    providing an aqueous sample in a large volume reservoir, said sample containing the analyte and having a volume of greater than or equal to 1 microliter, wherein the analyte is charged or has been associated with a charged molecule;
    electrophoresing the analyte from the large volume reservoir to a microfluidic device via a connector, wherein the microfluidic device comprises an analyis area, and the large volume reservoir and the microfluidic device are fluidically connected via the connector; and
    continuously flowing the analyte to the analysis area for a time sufficient to result in a higher concentration of the analyte in the analysis area than in the sample, wherein the analysis area comprises a capture site comprising a capture agent, and said method further comprises
    transporting the analyte across the capture site under conditions where the analyte is captured by the capture agent.

28. The method of claim 27, wherein said transporting across the capture site is by electrophoresis.

29. The method of claim 27, further comprising detecting the analyte hound by the capture agent.

30. The method of claim 27, wherein said sample has a volume of from 1 microliter to 100 mililiters.

31. The method of claim 30, wherein said sample has a volume of from 1 microliter to 20 mililiters.

32. The method of claim 27, further comprising providing at least one other aqueous sample in a large volume reservoir fluidically connected to the microfluidic device, the microfluidic device further comprising at least one other analysis area for said one other sample.

33. The method of claim 27, wherein said connector is a capillary tube.

34. A method for introducing an analyte of interest in a sample to a microfluidic device, comprising:
    providing an aqueous sample in a large volume reservoir, said sample containing the analyte and having a volume of greater than or equal to 1 microliter, wherein the analyte is charged or has been associated with a charged molecule;
    electrophoresing the analyte from the large volume reservoir to a microfluidic device via a connector, wherein the microfluidic device comprises an analyis area, and the large volume reservoir and the microfluidic device are fluidically connected via the connector; and continuously flowing the analyte to the analysis area for a time sufficient to result in a higher concentration of the analyte in the analysis area than in the sample, wherein the method further comprises immobilizing said analyte of interest on a microparticle before electrophoresis.

35. The method of claim 34, wherein said microparticle is a magnetic microparticle.

36. The method of claim 34, wherein said microparticle is coated with at least one receptor, antibody, or anti-ligand that specifically binds said analyte of interest or a group of molecules including said, analyte of interest.

37. The method of claim 36, wherein the method further comprises detecting a label on a second antibody bound to said analyte of interest or said group of molecules including said analyte of interest.

38. The method of claim 34, further comprising the step of removing the analyte from the microparticle prior to electrophoresis.

39. The method of claim 34, wherein said sample has a volume of from 1 microliter to 100 mililiters.

40. The method of claim 39, wherein said sample has a volume of from 1 microliter to 20 mililiters.

41. The method of claim 34, further comprising providing at least one other aqueous sample in a large volume reservoir fluidically connected to the microfluidic device, the microfluidic device further comprising at least one other analysis area for said one other sample.

42. The method of claim 34, wherein said connector is a capillary tube.

* * * * *